(12) United States Patent
Wang et al.

(10) Patent No.: US 11,837,044 B2
(45) Date of Patent: Dec. 5, 2023

(54) SYSTEM AND METHOD FOR NUTRITION TRACKING

(71) Applicants: Jun Wang, Xi'an (CN); Weijun Zhang, San Francisco, CA (US)

(72) Inventors: Jun Wang, Xi'an (CN); Weijun Zhang, San Francisco, CA (US)

(73) Assignee: Skoopin, San Jose, CA (US)

(*) Notice: Subject to any disclaimer, the term of this patent is extended or adjusted under 35 U.S.C. 154(b) by 528 days.

(21) Appl. No.: 17/152,786

(22) Filed: Jan. 19, 2021

(65) Prior Publication Data

US 2021/0383637 A1    Dec. 9, 2021

Related U.S. Application Data

(60) Provisional application No. 62/937,119, filed on Nov. 18, 2019, provisional application No. 62/937,129, (Continued)

(51) Int. Cl.
*G07F 13/04* (2006.01)
*G01G 19/414* (2006.01)
(Continued)

(52) U.S. Cl.
CPC ......... *G07F 13/04* (2013.01); *G01G 19/4146* (2013.01); *G06Q 30/0283* (2013.01); *G16H 20/60* (2018.01)

(58) Field of Classification Search
CPC ............... G07F 13/04; G01G 19/4146; G06Q 30/0283; G06Q 20/208; G16H 20/60
(Continued)

(56) References Cited

U.S. PATENT DOCUMENTS 6,024,281 A * 2/2000 Shepley .............. G06Q 20/343
                                                                    235/383
9,364,106 B1 * 6/2016 Ortiz ...................... B65D 25/04
(Continued)

FOREIGN PATENT DOCUMENTS

CN    104867081    *   8/2015
CN    109615777 A      4/2019
(Continued)

*Primary Examiner* — Jacques M Saint Surin
(74) *Attorney, Agent, or Firm* — AEON Law, PLLC; Adam L. K. Philipp; Shan Liao

(57) ABSTRACT

A nutrition tracking system comprises a nutrition tracking server, a plurality of weight-based food offering terminals, and one or more nutrition and meal information inquiry terminals. Multiple weight-based food offering terminals may be equipped on a food service cart. Each weight-based food offering terminal may be initialized to offer a type of food. The weight-based food offering terminal automatically measures the weight of food taken by a customer or for a customer, calculates the cost of food, and shows the weight and the cost on the display in real time. When the food is paid, the weight-based food offering terminal automatically reports the vending information to the nutrition tracking server. The nutrition tracking server maintains a database for customer meal information and a database for customer nutrition information. Customers may inquire their meal history and nutrition information using the nutrition and meal information inquiry terminals.

17 Claims, 11 Drawing Sheets

Related U.S. Application Data filed on Nov. 18, 2019, provisional application No. 62/937,124, filed on Nov. 18, 2019, provisional application No. 62/937,099, filed on Nov. 18, 2019.

(51) Int. Cl.
*G06Q 30/0283* (2023.01)
*G16H 20/60* (2018.01)

(58) Field of Classification Search
USPC ....................................................... 177/25.16
See application file for complete search history.

(56) References Cited

U.S. PATENT DOCUMENTS

| | | | |
|---|---|---|---|
| 10,971,031 B2* | 4/2021 | Ortiz | A47G 19/025 |
| 11,068,948 B1* | 7/2021 | Hanna | G06Q 30/0283 |
| 2007/0210154 A1 | 9/2007 | Suto | |
| 2014/0338987 A1 | 11/2014 | Kobres | |
| 2015/0100152 A1 | 4/2015 | Treviño et al. | |
| 2020/0233875 A1* | 7/2020 | Penev | G16H 20/60 |
| 2021/0035399 A1 | 2/2021 | Dai et al. | |
| 2021/0383341 A1 | 12/2021 | Wang et al. | |

FOREIGN PATENT DOCUMENTS

| | | |
|---|---|---|
| CN | 109658604 A | 4/2019 |
| CN | 109830041 A | 5/2019 |
| CN | 109872799 A | 6/2019 |
| CN | 111401103 A | 7/2020 |
| CN | 111402993 A | 7/2020 |
| WO | 2019132766 A1 | 7/2019 |

* cited by examiner

SYSTEM AND METHOD FOR NUTRITION TRACKING

CROSS-REFERENCE TO RELATED APPLICATIONS

This application claims priority to Provisional U.S. Patent Applications No. 62/937,099, No. 62/937,119, No. 62/937,124, and No. 62/937,129, filed Nov. 18, 2019, each of which is herein incorporated by reference in its entirety. This application further claims the benefit of foreign priority to applications filed in China No. 2019-10082279.5, No. 2019-10082278.0, No. 2019-10082277.6, No. 2019-10082263.4, filed Jan. 28, 2019, and No. 2019-10000642.4, No. 2019-10000643.9, filed Jan. 2, 2019, each of which is herein incorporated by reference in its entirety.

BACKGROUND OF THE INVENTION

Field of Invention

The present invention relates to the field of dietary information collection and, more particularly, to methods for nutrition tracking.

Background Art

Everyday people have been increasingly aware of the importance of a healthy diet. Instead of merely eating enough healthy food, more and more people realize the complexity of having a healthy and balanced diet: understanding the nutritional values of different food and managing caloric and nutritional intake. With the development of food science and big data, it has become more and more practical to obtain the detailed information on the ingredients in each prepared food/dish and analyze the nutritional composition of each meal. Food service especially room service has become popular in hotels, hospitals, sanatoriums, nursing homes, health centers, and rehabilitation centers. These customers have greater needs to pay attention to their nutritional intake. However, there is no existing technology to monitor and track the nutritional value of each meal with minimum effort from the users' perspective.

SUMMARY OF THE INVENTION

The present invention has been made to fulfill the above-mentioned need for tracking the nutritional intake in foods sold with food services. More specifically, the present invention utilizes a nutrition tracking system and a method of using weight-based food offering terminals for nutrition tracking. The nutrition tracking system tracks individual food service customer and their nutritional and meal information. Said nutritional and meal information is automatically generated using data analysis and processing technology and is based on the individual customer's food information collected at the weight-based food sales terminals. The system is capable of recording and retrieving the long-term nutritional intake information of the customer. The invention further comprises the nutrition tracking food service cart that can be used in restaurants, hotels, hospitals, sanatoriums, and other healthcare facilities.

The present invention provides solutions as follows:

The nutrition tracking system comprises a plurality of weight-based food offering terminals, a cloud-based nutrition tracking server, and one or more nutrition and meal information inquiry terminals. The weight-based food offering terminal s are connected to the cloud-based nutrition tracking server. The nutrition and meal information inquiry terminals are connected to the cloud-based nutrition tracking server. A weight-based food offering terminal collects the vending information for each customer and provides the information to the cloud-based nutrition tracking server, which then generates the corresponding nutrition and meal information that can be accessed by customers whenever they want via the inquiry terminals. The nutrition tracking system may further comprise one or more nutrition tracking food service carts.

The vending information for each customer by the weight-based food offering terminal includes at least the customer's ID, the name and the weight of food consumed, and the vending time. The cloud-based nutrition tracking server maintains the food ingredients information and ingredient nutrition facts information for each type of food. The cloud-based nutrition tracking server generates the customer's nutrition information based on the customer's vending information, the food ingredients information, and the nutrient information, where the customer's nutrition information includes at least the customer's ID, the name of the foods consumed, the dining time, and the intake of each ingredient and nutrient.

The weight-based food offering terminal stores the name of the food offered and automatically totals the weight of the food whenever it is consumed. The weight-based food offering terminal then records the dining time and reads the customer's ID and generates the corresponding vending information. The vending information comprises at least the customer's ID, the name and weight of the food consumed and the vending time. The vending information contains multiple vending information entries indexed by the customer's ID. The food ingredients information includes the name and the proportion of the ingredients used in the food. The nutrition facts information contains the name and proportion of the nutrients in each ingredient. The cloud-based nutrition tracking server calculates the nutrition information for each food according to the above information. The nutrition information contains at least the customer's ID, the name of foods consumed, the dining time, and the corresponding nutrient intakes. The nutrition information is also indexed by the customer's ID.

The weight-based food offering terminal includes the weighing and vending module, the accounting and payment module, the vending information storage module, the vending information display module, the primary network communication module, and the terminal information processing module. The weighing and vending module, the accounting and payment module, the vending information storage module and the vending information display module are connected to the terminal information processing module. The terminal information processing module is connected to the primary network communication module. The weighing and vending module calculates the total weight of the food vended using the weighing-by-difference method. The vending information storage module includes the food information storage unit and the vending information storage unit. The food information storage unit stores the food information such as the name and unit price information for the food, and the vending information storage unit stores the vending information. The terminal information processing module self-calculates the total price according to the weight and unit price information for the food consumed and sends the price to the accounting and payment module, which then displays the total price and payment information to customers, as well as obtaining the customer's ID and payment time after receiving the payment. The received ID and payment time information is then sent to the terminal information processing module, which then saves the payment time as the vending time and gathers the customer's ID, the vending time, the name and weight of the food vended, and the total price together to form the vending information and stores the information in the vending information storage unit. The vending information display unit indicates/displays the data from the terminal information processing module. The terminal information processing module sends the information stored in the storage modules, whenever being requested to do so or in a fixed time interval, to the cloud-based nutrition tracking server.

The weight-based food offering terminal further comprise detailed features related to methods of protecting the food that is offered, managing the access of food offered, identifying customers, managing the vending procedure, and handling payments.

The nutrition tracking system includes multiple weight-based food offering terminals, each being responsible for one type of food. The corresponding name and unit price information for the food is stored in the food information storage unit. Each weight-based food offering terminal has its unique ID and is connected to the cloud-based nutrition tracking server.

The cloud-based nutrition tracking server comprises a terminal food database, a customer meal database, a food ingredients database, a Nutrition Facts database, a server information processing module, a customer information inquiry module, a customer nutrition analysis module, a network communication module, and a customer nutrition database.

The terminal food database contains the food information for each weight-based food offering terminal. The food information includes multiple food information entries, each of which corresponds to the food sold by one weight-based food offering terminal. The food data comprises the ID of the weight-based food offering terminal, and the name and unit price of the food. The data is indexed by the weight-based food offering terminal's ID. The server information processing module updates the name and unit price information for each type of food in the food information storage unit as the corresponding value in the terminal food database whenever being requested to do so or in a fixed time interval. The customer meal database stores the basic information regarding customers' food consumption history. The customer's basic food information includes multiple food information entries indexed by customers' ID. Each customer basic food information includes the customer's ID, the name and weight of the food consumed, the total price and the dining time. The food information sent from each vending and weighting terminal is received by the server information processing module, which then sends and stores the information in the customer meal database.

The food ingredients database stores the food ingredients information for each type of food. The food ingredients information includes multiple food ingredients information entries, indexed by the name of the food. The entry includes the name of the food, the name and the proportion of the ingredients used in the food. The Nutrition Facts database stores the ingredients nutrition facts information. The customer nutrition database stores the nutrition information that comprises multiple nutrition information entries that are indexed by the customer's ID. Each nutrition information entry includes the customer's ID, the name of the foods, the dining time, and the name and intake of each nutrient. The customer's nutrition analysis module retrieves the weight of the food consumed from the customer meal information. It then multiplies the weight of the food consumed by the proportion of each ingredient to obtain the intake of the ingredient consumed. The nutrition analysis module then obtains the proportion of the nutrient in the ingredients from the Nutrition Facts database. The intake of each nutrient from one food can then be calculated by multiplying the intake of the ingredient by the proportion of the nutrient, and the total intake of the nutrient can be found as the sum of intakes from all ingredients and all foods. The customer's nutrition analysis module then gathers the customer's ID, the name of the food consumed, the dining time and the intake of nutrients together to form a nutrition information entry that is then saved to the customer nutrition database.

The nutrition and meal information inquiry terminal includes the nutrition and food information display module, the nutrition and meal information inquiry module and the network communication module. The nutrition and meal information inquiry module is connected to the nutrition and food display module and the tertiary network communication module. Customers may enter keywords that are sent by the tertiary network communication module to the secondary network communication module of the cloud-based nutrition tracking server. The secondary network communication module then sends the keywords to the nutrition and meal information inquiry module, which searches the data stored in the customer nutrition database and/or the customer's food information database. The results are then sent back to and displayed by the nutrition and food display module via the secondary and tertiary network communication.

The nutrition tracking mobile food cart is equipped with a power management module that can be connected to the rechargeable battery set or a power supply. The nutrition tracking mobile food cart is equipped with multiple vending terminal holders on which the weight-based food offering terminals are mounted. Each weight-based food offering terminal is used to offer one type of food. The weight-based food offering terminals are connected to the power management module.

The present invention provides the following unique solutions and features:

1. The present invention integrates a nutrition tracking system, a plurality of weight-based food offering terminals. The nutrition tracking system generates the unique food and nutrition information for each customer based on the collected data and records and analyzes customers' long-term diet and nutrition intake, which provides convenient means for customers to understand their diet and nutrition intake.

2. The invention further comprises a nutrition tracking mobile food delivery cart that can be widely applied in hotels, hospitals, sanatoriums, and other healthcare facilities.

BRIEF DESCRIPTION OF THE DRAWINGS

The accompanying drawings, which are incorporated in and constitute a part of the specification, illustrate embodiments of the invention and together with the description, serve to explain the principles and structures of the invention.

DETAILED DESCRIPTION OF INVENTION

The following description presents various embodiments of the present invention. They are presented by way of examples, and not limitations.

An embodiment of the present invention comprises a nutritional tracking system that can track a user's meal. In one preferred embodiment, a tracking means is installed in a food service cart, which is especially suitable in applications in restaurants, hotels, hospitals, sanatoriums and other healthcare facilities. Therefore, a preferred embodiment of the present invention comprises a food service cart with nutrition tracking means for restaurants, hotels, hospitals, sanatoriums and other healthcare environment.

Figure 1:
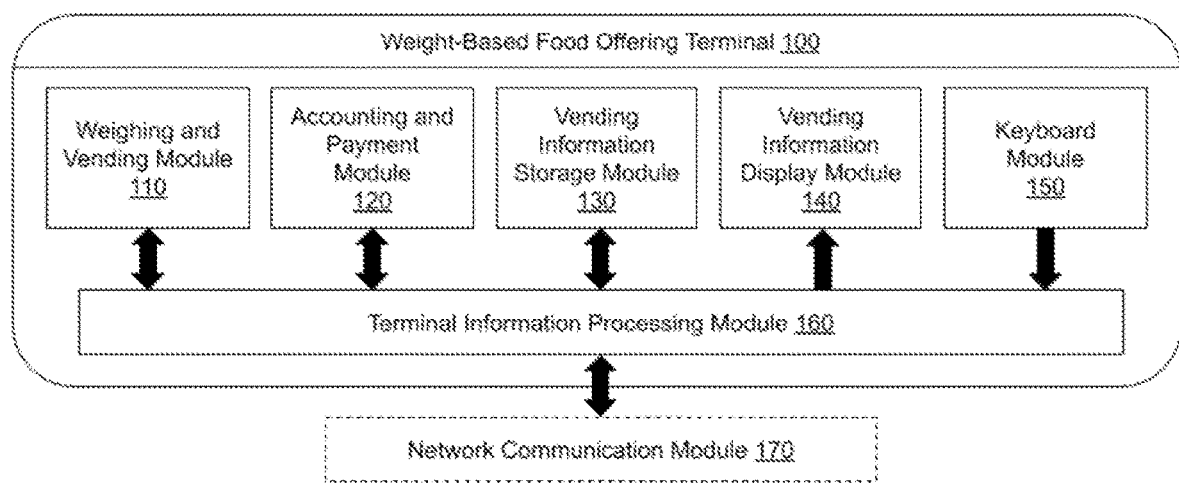
FIG. 1 illustrates a block diagram of a weight-based food offering terminal in accordance with an embodiment of the present invention.
Figure 2:
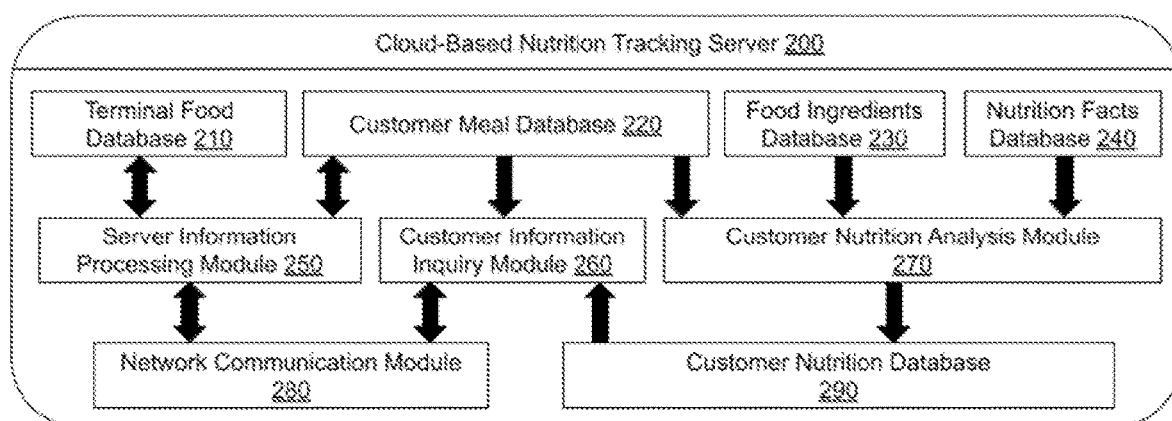
FIG. 2 illustrates a block diagram of a cloud-based nutrition tracking server in accordance with an embodiment of the present invention.
Figure 3:
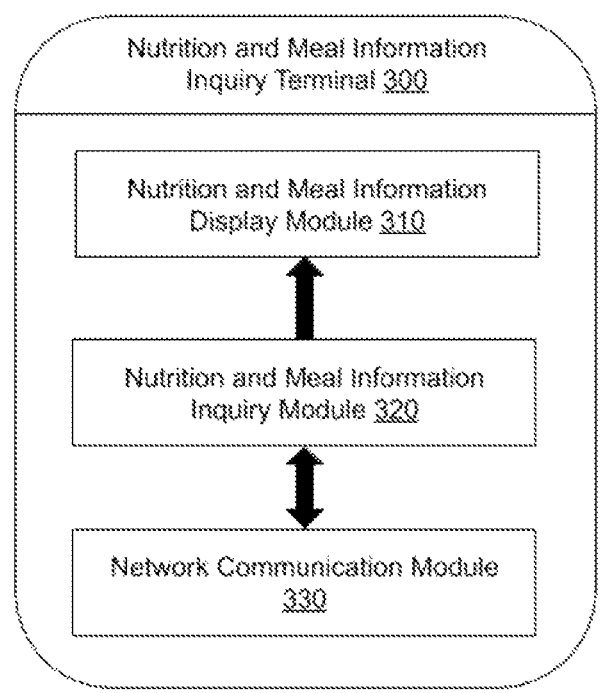
FIG. 3 illustrates a block diagram of a nutrition and meal information inquiry terminal in accordance with an embodiment of the present invention.

The following is a detailed description of a nutrition tracking system and a food service cart in accordance with an embodiment of the present invention. The food service cart is equipped with a nutrition and meal monitoring and tracking means and is considered as a preferred extended application of the nutrition tracking system; but is not intended to limit the present invention to the nutrition tracking food service cart. As shown in FIGS. 1-3, the present invention includes a weight-based food offering terminal (as known as a weighing and vending terminal/unit), a cloud-based nutrition tracking server, and a nutrition and meal information inquiry terminal. Three parts are connected preferably via a wireless connection for data communication. Each part is described in detail below.

A. Weight-Based Food Offering Terminal

In one preferred embodiment, one weight-based food offering terminal may offer one type of food. A type of food can be any kind of prepared food: meat, fish, dairy, stew, stir fry, bread, rice, pasta, salad, fruits, dessert, cookies, soup, or beverage, etc. Typically, a type of food is an item on a restaurant menu and the like. The weight-based food offering terminal can automatically measure an amount of food sold by weight for each sale. And it automatically calculates the cost of each sale.

As illustrated in FIG. 1, a weight-based food offering terminal 100 comprises a weighing and vending module 110, an accounting and payment module 120, a vending information storage module 130, a vending information display module 140, a keyboard module 150, and a terminal information processing module 160. The weight-based food offering terminal 100 may further comprise a network communication module 170. The weighing and vending module 110, the accounting and payment module 120, the vending information storage module 130, the vending information display module 140 and the keyboard module 150 are each connected to the terminal information processing module 160, which is linked to the network communication module 170.

The terminal information processing module 160 is a central processing unit for information processing and data communication with other connected modules. Its main functions include: For each transaction at the weight-based food offering terminal 100, it automatically calculates a cost of food (amount due) according to a weight of food taken by a customer (or for a customer) and a unit price for the food, wherein the weight of the food taken is from the weighing and vending module 110, and the unit price for the food is from the vending information storage module 130; and sends the obtained cost of the food to the accounting and payment module 120. At the same time, it sends the weight and the cost of the food taken to the vending information display module 140 for displaying the information to a customer. When the customer pays, the terminal information processing module 160 obtains the corresponding customer's ID and a payment time from the accounting and payment module 120, it combines the customer's ID, the payment time, the weight and price of the food sold, and the name of the food to form a customer specific entry of vending information record to be stored in the vending information storage module 130, and further sends the customer specific entry of vending information record to a nutrition tracking server via the network communication module 170.

The accounting and payment module 120 can automatically generate the amount due to be paid by the customer according to the cost of the food sold provided by the terminal information processing module 160, and hence settle the payment amount. For example, when a customer completes a payment using a credit card or a debit card, the accounting and payment module 120 automatically generates the corresponding amount due instruction against the card. When a customer completes a payment using an online payment platform like WeChat or Alipay, the accounting and payment module 120 automatically generates and sends the corresponding amount due information to the online payment platform or a corresponding payment terminal. In particular, the accounting and payment module 120 supports the password-less authentication or auto-debit service empowered by online payment platforms like WeChat or Alipay. When interacting with a customer, the accounting and payment module 120 collects the customer identification (i.e. the customer's ID) and the payment time (i.e. the vending time) and sends the collected information to the terminal information processing module 160. The above accounting and payment module 120 supports credit/debit card payment and online payments such as WeChat or Alipay.

The vending information display module 140 is used to display or indicate the customer's purchase and payment module 110, and vending information of each customer. The vending information storage module 130 preferably includes the food information storage unit and the vending information storage unit. The food information storage unit stores food information comprising food name (which represent the type of food) and the corresponding food unit price. The vending information storage unit stores the vending information for each customer, comprising food name, weight of food sold, food cost, customer ID and payment time (i.e., vending time). The vending information is indexed by the customer's ID as the vending information records illustrated in the following Table 1, Vending Information Table:

TABLE 1

| Vending Information | Customer ID1 | Food name | Weight of food sold | Food cost | Vending time | ... |
|---|---|---|---|---|---|---|
| | Customer ID2 | Food name | Weight of food sold | Food cost | Vending time | ... |
| | ... | ... | ... | ... | ... | ... | information, wherein the data is obtained from the terminal information processing module 160. The information to be displayed includes the name and the unit price of the food that the terminal information processing module 160 retrieves from the vending information storage module 130, and the weight and the cost of the food sold after the customer takes some of the food.

The keyboard module 150 provides manual input operation for the weight-based food offering terminal 100. The operation includes data initialization, interaction and startup operation with the cloud-based nutrition tracking server, and manual options of data and selections to be displayed by the vending information display module 140.

Figure 4:
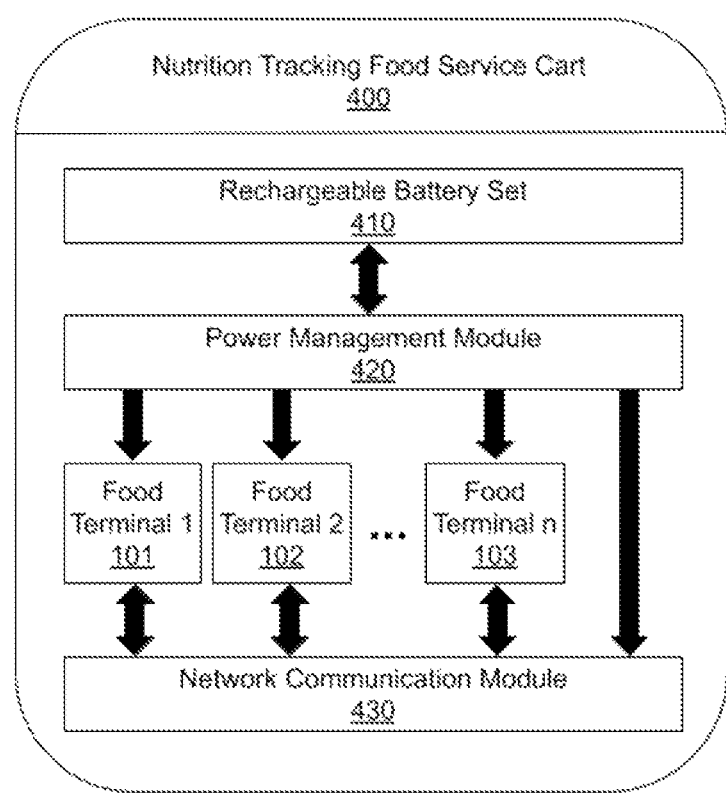
FIG. 4 illustrates a block diagram of a nutrition tracking food service cart in accordance with an embodiment of the present invention.

The network communication module 170 is used for data communication between the weight-based food offering terminal 100 and the cloud-based nutrition tracking server. The data from each module in the weight-based food offering terminal 100 is sent to the cloud-based nutrition tracking server. Preferably, when the meal and nutrition tracking system is applied to a food service dart, one or more weight-based food offering terminal 100s may be equipped on a food service cart and can share the same network communication module 170. As illustrated in FIG. 4, it is not necessary for each weight-based food offering terminal 100 to have its own network communication module 170.

A preferred embodiment of the above weighing and vending module 110 automatically calculates the weight of food sold based on a weighing by difference technique. The weighing and vending module 110 is preferably equipped with a weighing-by-difference tray and a weighting-by-difference scale. The food to be sold is placed on the weighing-by-difference tray. The weighing-by-difference scale is mounted beneath the weighing-by-difference tray. The weight of food sold is calculated as the difference between the initial weight of the food (the initial weight is updated each time when some food is sold) and the weight on the tray after some food is taken. The obtained weight of food sold is sent to the terminal information processing module 160. Other weight calculation approaches may also be used as long as the weight of food sold can be automatically computed and sent to the terminal information processing module 160.

The vending information storage module 130 stores information about the food handled by the weighing and vending The name and the unit price of the food in the food information storage unit are retrieved from the cloud-based nutrition tracking server. The customer's ID (i.e., identification) contains unique identification information for each customer and can be entered into the system via the keyboard module 150 or retrieved from the accounting and payment module 120. Particularly when the customer completes a payment by swiping a card or using WeChat or Alipay, the accounting and payment module 120 automatically reads the card identification from the customer's card or the payer's user identification from the customer's online payment account. Such card identification or user identification is uniquely linked to the customer identification. The name of the food is retrieved from the food information storage unit. The weight of the foods sold is acquired from the weight and vending module. The cost of the food sold is calculated based on the weight and the unit price of the food by the terminal information processing module 160. The payment time is the time when the customer made the payment via the accounting and payment module 120. The payment time is provided by the accounting and payment module 120.

Following are exemplary operations carried out by a weight-based food offering terminal 100.

1) During a power-on reboot or a data initialization via the keyboard, the terminal information processing module 160 of the above weight-based food offering terminal 100 requests for downloading the food information (name and unit price) to the cloud-based nutrition tracking server and stores the downloaded food information in the food information storage unit of the vending information storage module 130. The saved food name and unit price information is then sent to the vending information display module 140, which then displays the information to customers. Therefore, the weight-based food offering terminal 100 displays the name and the unit price of the food being offered.

2) The food being offered on the weight-based food offering terminal 100 is placed on the weighing-by-difference tray. After a customer has taken a desired amount of food, the weighing and vending module 110 can calculate the amount of food taken by the customer as the weight difference between the detected food weight on the tray before the customer taking food and the detected food weight on the tray after the customer taking food. The obtained weight amount is then sent to the terminal information processing module 160. The terminal information processing module 160 multiplies the received weight amount by the corresponding food unit price stored in the vending information storage module 130 to determine the cost of food taken by the customer, i.e., the amount due. The amount due is to be sent to the accounting and payment module 120 that handles the payment. The terminal information processing module 160 sends the weight and the cost of the food to the vending information display module 140, which then displays the information to the customer. This way, the customer gets the instant feedback about the amount (weight) of food and the cost of food that he/she has taken from the tray.

3) The accounting and payment module 120 receives the amount due from the terminal information processing module 160. When the customer pays by swiping a card, the accounting and payment module 120 generates a payment instruction against the customer's card account and interacts with the customer to complete the payment transaction. When the customer uses an online payment platform (for example, WeChat or Alipay) to pay, the accounting and payment module 120 generates a payment instruction to a user terminal and interacts with the customer to complete the payment transaction. The accounting and payment module 120 may support the password-less authentication or auto-debit service empowered by online payment platforms like WeChat or Alipay. When the accounting and payment module 120 interacts with the customer during the payment process, it also automatically reads the customer's unique ID information, records the payment time, and sends them to the terminal information processing module 160.

4) After receiving the customer's ID and payment time, the terminal information processing module 160 combines the customer's ID, the payment/vending time, the food name, the weight and the cost of the food sold to form a vending information entry. The vending information entry is then stored in the vending information storage unit. Because each weight-based food offering terminal 100 only offers one type of food, the terminal information processing module 160 automatically generates and stores a customer specific entry for this type of food after each time the customer finishes taking this type of food. The time is the payment time when the customer's ID and payment time is received from the accounting and payment module 120, which indicates the customer has finished taking food and paid for this type of food. The vending information entries in the vending information storage unit form a complete set of vending information as illustrated in the above table 1.

5) Finally, the terminal information processing module 160 uploads the food information and the vending information to a nutrition tracking server via the network communication module 170 in real-time.

A weight-based food offering terminal 100 further comprise detailed features related to methods of protecting the food that is offered, managing the access of food offered, identifying customers, managing the vending procedure, and handling payments. These features are depicted in FIGS. 5-13 and described in Section E. More Detailed Description of Weight-based Food Offering Terminal.

B. Cloud-Based Nutrition Tracking Server

A nutrition tracking server can serve multiple weight-based food offering terminals 100. As illustrated in FIG. 2, a cloud-based nutrition tracking server 200 comprises a terminal food database 210 (also known as a vending terminal's meal information database), a customer meal database 220 (also known as a customer's basic meal information database), a food ingredients database 230 (also known as a content of ingredient information database), a Nutrition Facts database 240 (also known as a content of nutrient information database), a server information processing module 250 (also known as a cloud information processing and transmission module), a customer information inquiry module 260 (also known as a customer's meal and nutrition information inquiry module), a customer nutrition analysis module 270 (also known as a customer's nutrition processing and analysis module), a network communication module 280, and a customer nutrition database 290 (also known as a customer's nutrition information database). The terminal food database 210 and the customer meal database 220 are connected to the server information processing module 250. The customer meal database 220 is also connected to the customer information inquiry module 260 and the customer nutrition analysis module 270. The food ingredients database 230 is connected to the customer nutrition analysis module 270. The server information processing module 250 and the customer information inquiry module 260 are connected to the network communication module 280. The customer information inquiry module 260 and customer nutrition analysis module 270 are connected to the customer nutrition database 290.

The terminal food database 210 stores the name and unit price information for food offered at each weight-based food offering terminal 100. The terminal food information is indexed by an ID of each weight-based food offering terminal, wherein the ID uniquely identifies a weight-based food offering terminal. A preferred data format of recording terminal food information is illustrated in Table 2, Terminal food information table:

TABLE 2

| Terminal Food Information | weight-based food offering terminal ID1 | Name of food 1 | Unit price 1 |
|---|---|---|---|
| | weight-based food offering terminal ID2 | Name of food 2 | Unit price 2 |
| | weight-based food offering terminal ID3 | Name of food 3 | Unit price 3 |
| | ... | ... | ... |

When a weight-based food offering terminal 100 is powered on or initiated by keyboard instructions, it sends a request for updating food information to the server information processing module 250. The server information processing module 250 locates a food name and unit price information according to the corresponding weight-based food offering terminal ID. The server sends the food name and unit price information to the weight-based food offering terminal 100 via the network communication module 280. The weight-based food offering terminal 100 then stores the food information in its own vending information storage module 130. This completes the update of food information at the weight-based food offering terminal 100.

The customer meal database 220 contains customer meal information that comprises vending information entries from multiple weight-based food offering terminals. Each weight-based food offering terminal uploads vending information stored in its vending information storage module to the server 200 in real-time, periodically, or when requested by the server 200. The cloud-based nutrition tracking server 200 receives uploaded vending information in real-time via the network communication module 280 and the server information processing module 250 and stores the uploaded vending information in the customer meal database 220. This generates customer meal information. Each customer's meal information entry combines all vending information records associated with said customer. A customer meal information entry comprises a customer's ID and one or more food-dining time sub-entries, wherein each food-dining time sub-entry further comprises a food name, a food weight, a food cost, and a dining time (i.e., vending time), as illustrated in the following table 3, Customer Meal

TABLE 3

| Customer Meal Information | Customer ID1 | Food Name 1 | Food Weight | Food Cost | Dining Time | ... |
|---|---|---|---|---|---|---|
| | | Food Name 2 | Food Weight | Food Cost | Dining Time | ... |
| | | Food Name 3 | Food Weight | Food Cost | Dining Time | ... |
| | | ... | ... | ... | ... | ... |
| | Customer ID2 | Food Name I | Food Weight | Food Cost | Dining Time | ... |
| | | Food Name II | Food Weight | Food Cost | Dining Time | ... |
| | | Food Name III | Food Weight | Food Cost | Dining Time | ... |
| | | ... | ... | ... | ... | ... |
| ... | ... | ... | ... | ... | ... | ... |

The above customer meal information entries are based on vending information entries provided by weight-based food offering terminals and are organized by the customer ID field. The mapping between vending information entry fields and customer meal information entry fields: vending information "Customer ID" field is mapped to customer meal information "Customer ID" field, vending information's "Food name" field, "Weight of food sold" field, "Food cost" field, and "Vending time" field are mapped to corresponding food-dining time sub-entry's "Food Name" field, "Food Weight" field, "Food Cost" field and "Dining Time" field. The server information processing module 250 stores and updates the data in the customer meal database 220.

The food ingredients database 230 contains food ingredients information, organized by food names. Each food has one or more ingredients and their corresponding percentages as illustrated in below Table 4, Food Ingredients Information Table.

TABLE 4

| Food Ingredients Information | Food Name 1 | Ingredient 1 | Percentage |
|---|---|---|---|
| | | ingredient 2 | Percentage |
| | | Ingredient 3 | Percentage |
| | | ... | ... |
| | Food Name 2 | Ingredient I | Percentage |
| | | Ingredient II | Percentage |
| | | Ingredient III | Percentage |
| | | ... | ... |
| | ... | ... | ... |

The food ingredients database 230 contains entries for all types of foods that are offered in the nutrition tracking system. Each type of food has an ingredients information entry, comprising a food name, each ingredient in the food and corresponding weight percentage of said ingredient. The data in the food ingredients database 230 may be entered during an initialization. The data may be obtained by analyzing each type of food in advance.

The Nutrition Facts database 240 contains nutrition facts information, organized by ingredient names. Each ingredient entry has one or more nutrients and their corresponding percentages as illustrated in below Table 5, Nutrition Facts Information Table.

TABLE 5

| Nutrition Facts Information | Ingredient Name 1 | Nutrient 1 | Percentage |
|---|---|---|---|
| | | Nutrient 2 | Percentage |
| | | Nutrient 3 | Percentage |
| | | ... | ... |
| | Ingredient Name 2 | Nutrient I | Percentage |
| | | Nutrient II | Percentage |
| | | Nutrient III | Percentage |
| | | ... | ... |
| | ... | ... | ... |

The Nutrition Facts database 240 contains nutrition facts about all types of ingredients that are used in the nutrition tracking system. Each ingredient has a nutrition facts entry, comprising ingredient name, each nutrient in the ingredient and corresponding weight percentage of said nutrient. The nutrition facts data may be measured in advance and be entered into the database during an initialization.

The customer nutrition database 290 stores the data regarding customers' dietary nutrition information. The data is generated by the customer nutrition analysis module 270 based on data stored in the customer meal database 220, the food ingredients database 230 and the Nutrition Facts database 240. In one scenario, the customer nutrition analysis module 270 first retrieves a customer specific data entry from the customer meal database 220. Each customer specific data entry comprises customer ID and one or more food-dining time sub-entries. Each food-dining time sub-entry comprises a food name, a food weight, a food cost, and a dining time. For each food-dining time sub-entry, the customer nutrition analysis module 270 retrieves the food ingredients information entry from the food ingredients database 230. The customer nutrition analysis module 270 multiplies the weight of the food by the percentage of each ingredient to calculate an amount of each ingredient. Next, for each ingredient in the ingredients information entry, the customer nutrition analysis module 270 retrieves the corresponding nutrition facts entry from the Nutrition Facts database 240. The customer nutrition analysis module 270 calculates a quantity of each nutrient in each ingredient by multiplying the amount of each ingredient by the percentage of said nutrient in said ingredient. Then for each type of nutrient, the customer nutrition analysis module 270 sums the quantities of said nutrient in all ingredients in said food to calculate a nutrient intake in said food weight amount of said food. Lastly the customer nutrition analysis module 270 generates a customer specific dietary nutrition information entry and stores updates it in the customer nutrition database 290. The customer dietary nutrition information entries in the customer nutrition database 290 are indexed by customer IDs. Its format is illustrated in below Table 6, Customer Dietary Nutrition Information Table:

TABLE 6

| Customer Dietary Nutrition Information | Customer ID 1 | Food 1 | Nutrient 1 | Nutrient 1 Intake | Dining Time | ... |
|---|---|---|---|---|---|---|
| | | | Nutrient 2 | Nutrient 2 Intake | | |
| | | | Nutrient 3 | Nutrient 3 Intake | | |
| | | | ... | ... | | |
| | | Food 2 | Nutrient 1 | Nutrient 1 Intake | Dining Time | ... |
| | | | Nutrient 2 | Nutrient 2 Intake | | |
| | | | Nutrient 3 | Nutrient 3 Intake | | |
| | | ... | ... | ... | ... | ... |
| | Customer ID 2 | Food I | Nutrient 1 | Nutrient 1 Intake | Dining Time | ... |
| | | | Nutrient 2 | Nutrient 2 Intake | | |
| | | | Nutrient 3 | Nutrient 3 Intake | | |
| | | | ... | ... | | |
| | | Food II | ... | ... | Dining Time | ... |
| | | | ... | ... | | |
| | | | ... | ... | | |
| | Customer ID 3 | ... | ... | ... | ... | ... |
| | ... | ... | ... | ... | ... | ... |

The dining times in a customer dietary nutrition information entry in the customer nutrition database 290 are the corresponding dining times in the same customer's meal information entry in the customer meal database 220. This way, after the customer nutrition analysis module 270 finishes processing all the data entries in the customer meal database 220 using the information from the food ingredients database 230 and the Nutrition Facts database 240, the customer nutrition database 290 has all customers' dietary nutrition information: for each customer, a dietary nutrition information entry comprises a customer ID, one or more subentries of food name, a list of nutrients and their corresponding intakes, and dining time.

The customer information inquiry module 260 retrieves a customer's meal and/or nutrition information from the customer meal database 220 and the customer nutrition database 290, upon receiving a request from a nutrition and meal information inquiry terminal. The information is processed and organized before being sent to the nutrition and meal information inquiry terminal via the network communication module 280.

When the customer information inquiry module 260 receives a request for a customer's meal information from a nutrition and meal information inquiry terminal, it searches the customer meal database 220 according to the customer's ID, process the query results, and sends the processed query results to the nutrition and meal information inquiry terminal. For example, when an inquiry is about a customer's meal information during a particular time period, the corresponding request contains the customer's ID and the time period. The customer information inquiry module 260 filters all the meal data of this customer in the customer meal database 220 and sends the customer's meal information within the time period to the nutrition and meal information inquiry terminal.

When the customer information inquiry module 260 receives a request for a customer's nutrition information from a nutrition and meal information inquiry terminal, it searches the customer nutrition database 290 according to the customer's ID, process the query results, and sends the processed query results to the nutrition and meal information inquiry terminal. For example, when an inquiry is about a customer's nutrition information during a particular time period, the corresponding request contains the customer's ID and the time period. The customer information inquiry module 260 filters all the dietary nutrition data of this customer in the customer nutrition database 290 and sends the customer's dietary nutrition information within the time period to the nutrition and meal information inquiry terminal.

In a preferred embodiment, the customer information inquiry module 260 can further process query results regarding meal and nutrition information, for example, combining data regarding a same nutrient from one or more data records. In a particular example, the customer information inquiry module 260 can sum the quantities of a type of nutrient intake and send the sum to a nutrition and meal information inquiry terminal. This kind of further processing brings clarity to inquiry results especially when the inquiries are for a particular customer ID.

Following are the exemplary major steps that the cloud-based nutrition tracking server 200 performs according to its functional modular structure.

1) An administrator initializes the configuration regarding the terminal food information (including the name and unit price information for the different foods on different weight-based food offering terminals) stored in the terminal food database 210.

2) When a weight-based food offering terminal is powered on (or initiated via keyboard instructions), the weight-based food offering terminal retrieves its food name and unit price information from the nutrition tracking server: the food name and unit price information is obtained from the terminal food database 210 according to the terminal's ID and is sent to the corresponding weight-based food offering terminal via the server information processing module 250 and the network communication module 280.

3) The server information processing module 250 receives real time vending information from the weight-based food offering terminals via the network communication module 280 and stores the information in the customer meal database 220.

4) The costumer nutrition analysis module 270 retrieves costumer meal information (includes food name, food weight, customer ID, and dining time) from the customer meal database 220.

5) For each food name in a costumer meal information entry, the customer nutrition analysis module 270 calculates the weight of each ingredient in the food: retrieving corresponding food ingredients information entry from the food ingredients database 230 according to the food name; multiplying the food weight by the percentage of each ingredient in the food ingredients information entry.

6) For the above each food, according to the ingredients in said food obtained in step 5), the customer nutrition analysis module 270 retrieves their nutrition facts entries from the Nutrition Facts database 240. The customer nutrition analysis module 270 calculates a quantity of each nutrient in each ingredient by multiplying the weight of said each ingredient by the percentage of said nutrient in said each ingredient. Then for each type of nutrient, the customer nutrition analysis module 270 sums the quantities of said nutrient in all ingredients in said food to calculate a nutrient intake in said food. This way, the customer nutrition analysis module 270 calculates the amount of each nutrient that the customer gets from eating said food.

7) The customer nutrition analysis module 270 repeats steps 5) and 6) until all nutrient intakes from all the foods that all customers have eaten been determined. The customer nutrient intake information is then organized to customer dietary nutrition information indexed by the customer IDs and is stored in the customer nutrition database 290. A customer dietary nutrition information entry comprises a customer ID, food names, dining times, nutrients, and their intakes.

8) The customer information inquiry module 260, upon receiving a request from a nutrition and meal information inquiry terminal, searches the requested nutrition information from the customer nutrition database 290 and/or the request meal information from the customer meal database 220. The information is processed and then sent to the nutrition and meal information inquiry terminal via the network communication module 280.

C. Nutrition and Meal Information Inquiry Terminal

As illustrated in FIG. 3, a nutrition and meal information inquiry terminal 300 comprises a nutrition and meal information display module 310, a nutrition and meal information inquiry module 320, and a network communication module 330. The nutrition and meal information inquiry module 320 is connected to the nutrition and meal information inquiry display module 310 and the network communication module 330. A customer may enter an inquiry via the nutrition and meal information inquiry module 320, which sends the entered inquiry to a nutrition tracking server via the network communication module 330. The nutrition tracking server sends a search result, to the nutrition and meal information inquiry module 320, which then displays the result on the nutrition and meal information display module 310. In one preferred embodiment, the nutrition and meal information inquiry terminal 300 is integrated into a customer's mobile device.

D. Nutrition Tracking Food Service Cart

In another preferred embodiment, the present invention further comprises a nutrition tracking food service cart that uses the above nutrition tracking system. As illustrated in FIG. 4, a nutrition tracking food service cart 400 is equipped with one or more weight-based food offering terminals 101, 102, and 103, (i.e., in short, food terminal 1, food terminal 2, and food terminal n in FIG. 4), each of which offers one type of food. The multiple weight-based food offering terminals are connected to a power management module 420, which is preferably connected to a rechargeable battery set 410. In this way, the food service cart is powered with or without an external power supply. Alternatively, the food service cart may also be powered by an external power supply only, i.e., the rechargeable battery set 410 may be replaced by a power connector. The power management module 420 has the following functions:

When the food service cart 400 is powered by an external supply, the power management module 420 controls the external power supply to power the weight-based food offering terminals (101, 102, 103, . . . ) and the wireless network communication module 430, as well as charge the rechargeable battery set 410.

When the food service cart 400 is not connected to an external supply, the power management module 420 controls the rechargeable battery set 410 to power the weight-based food offering terminals (101, 102, 103, . . . ) and the wireless network communication module 430.

The multiple weight-based food offering terminals (101, 102, 103, . . . ) may share the network communication module 430 to communicate with a nutrition tracking server, preferably via a wireless network. Alternatively, the multiple weight-based food offering terminals (101, 102, 103, . . . ) may have their own independent network communication modules and therefore wirelessly communicate with a nutrition tracking server independently.

In a particular embodiment the food service cart 400 is a mobile cart with multiple weight-based food offering terminals. The mobile cart is portable and may be moved manually.

E. More Detailed Description of Weight-Based Food Offering Terminal

A weight-based food offering terminal 100 described in Section A. Weight-based Food Offering Terminal, may further comprise more features related to methods of protecting the food that is offered, managing the access of food offered, identifying customers, managing the vending procedure, and handling payments. These features are depicted in FIGS. 5-13 and described in the current Section E. More Detailed Description of Weight-based Food Offering Terminal.

A weight-based self-checkout vending apparatus in accordance with one embodiment of the present invention is used as a weight-based food offering terminal 100.

The weight-based self-checkout apparatus works like an improved vending machine for food. A customer can freely choose any amount of food. The self-checkout apparatus uses a weighing-by-difference method to automatically display the cost of food taken by a customer, allowing the customer to pay by a credit/debit card, using WeChat to read a QR code, or using other online payment methods like Alipay, etc.

In a further embodiment of the present invention, the control panel of the self-checkout vending apparatus has a code scan area. The code scan area has a QR code or a QR code reader, which supports payments via WeChat and Alipay. When the central processing unit receives a signal based on a customer scan activity, the central processing unit unlocks a door or controls an actuator to open a product access window so that the customer can get the desired goods. When the central processing unit receives a completion signal or successful completion of payment, the central processing unit locks the door or controls an actuator to close the product access window.

In a further embodiment of the present invention, the self-checkout vending apparatus is connected to an external operating and accounting platform that includes an accounting module and an operation identification module. The self-checkout vending apparatus comprises a code scan area which has a QR code or QR code reader. When sensing a scanning activity, the operation identification module sends a request for access to goods to the central processing unit via a signal transceiver. When finished, the central processing unit generates and sends payment details to the accounting module, which then settles the payment accordingly.

The self-checkout vending apparatus comprising a product tray, integrated load cells, a central processing unit, and a means to control the access to goods offered. In one preferred embodiment, a card reader's successful reading of a customer's card opens the access to the goods offered. In an alternative preferred embodiment, a customer may use a mobile device to scan a code on the self-checkout vending apparatus to gain the access to the good offered.

The integrated load cells measure the weight of the goods on the product tray and sends the updated weight measurement to the central processing unit in real time. As a customer getting an amount of goods, the weight of the goods taken is calculated by the central processing unit as the difference of the weights of the goods on the product tray before and after the customer getting the amount of goods. The central processing unit calculate a cost of the goods taken based on the weight of the goods taken and the unit price of the goods. After the customer pays for the goods taken, the access to the goods offered is closed.

The central processing unit of the self-checkout vending apparatus controls a data storage that maintains the initial weight of goods on each product tray and their unit price information. The unit price information is entered into the data storage system when the goods are replenished. The initial weight is updated using the most recent weight of the remaining goods after each time a purchase is made.

A self-checkout vending apparatus in accordance with the present invention holds goods on one or more product trays. The product trays may hold different types of goods with different unit prices. Load cells are mounted under each product tray and can measure the weight of the goods on each product tray in real time. A user may use a card or an online payment app to unlock/open the vending apparatus and to initiate a purchase. The central processing unit checks if the vending apparatus is out of stock based on the current weight of goods on the one product tray or the current total weight on all the product trays. If out-of-stock, an alert is triggered and transmitted by the central processing unit. The user may take any desired amount of goods from any tray. The apparatus automatically detects the type of goods and the weight amount taken by the user and calculates the total cost. After the user payment, the apparatus automatically resets the initial weight of the goods on each product tray and gets ready for the next purchase.

Figure 5:
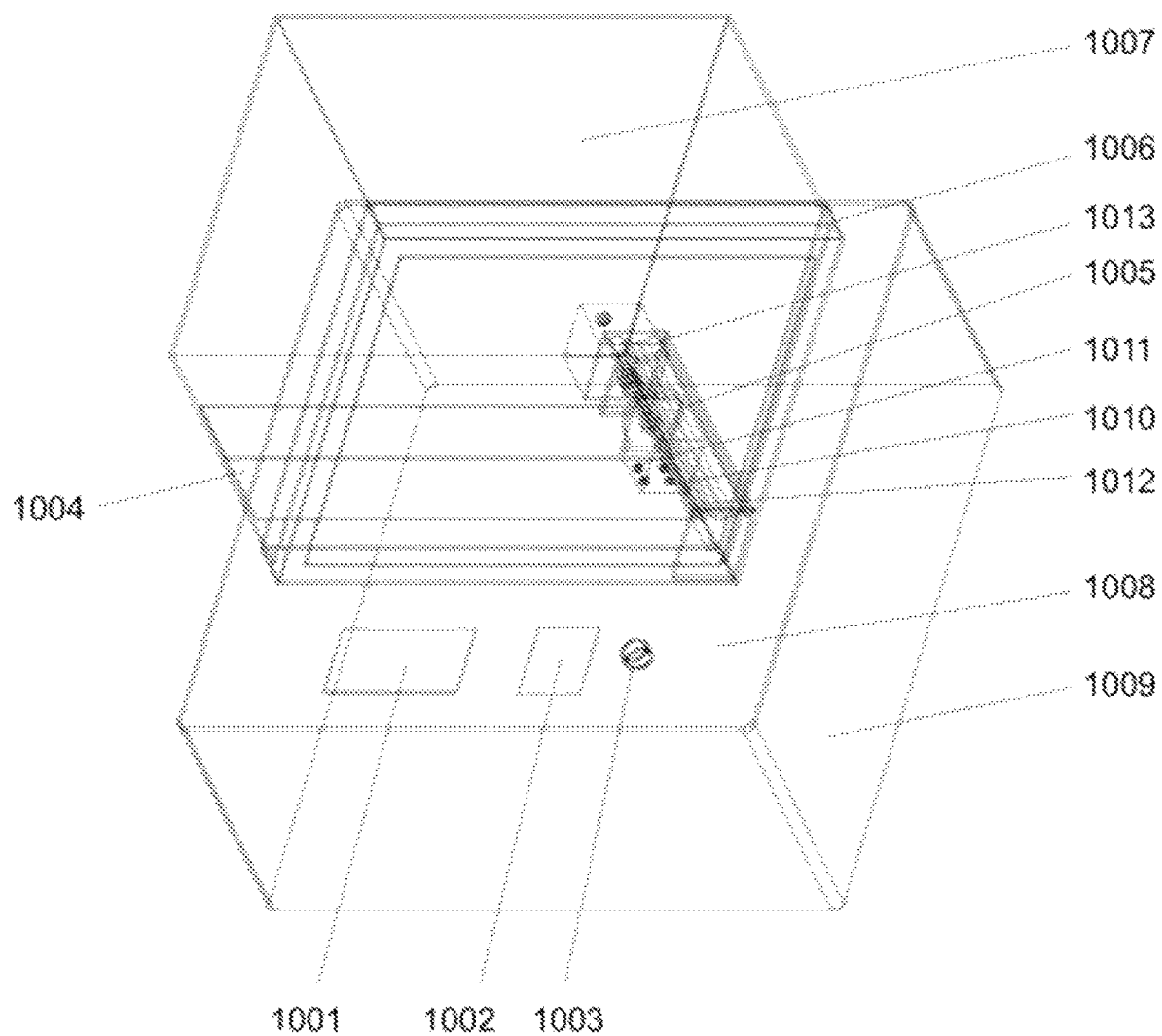
FIG. 5 illustrates a schematic view of a weight-based self-checkout vending apparatus in accordance with a first embodiment of the present invention.
Figure 6:
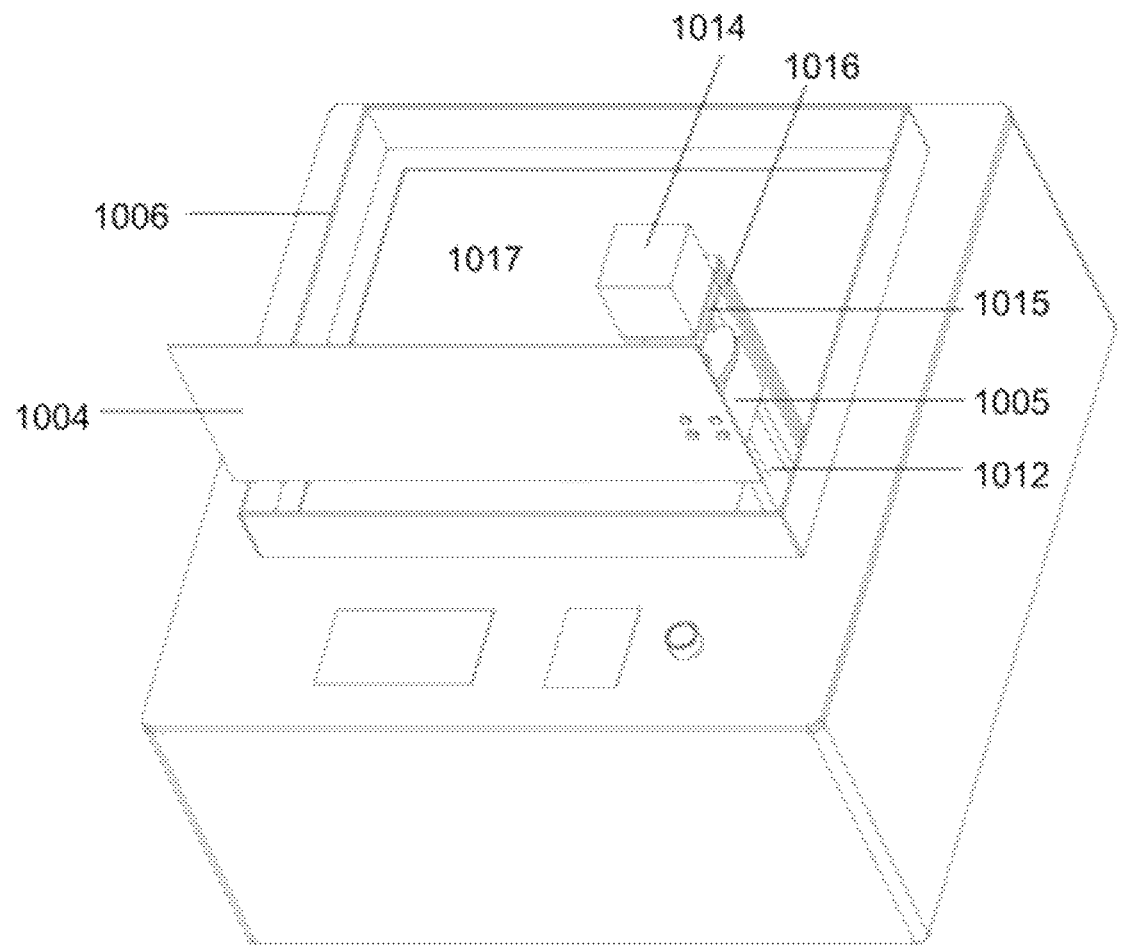
FIG. 6 illustrates the schematic view of the weight-based self-checkout vending apparatus in accordance with the first embodiment of the present invention and with a protective shield removed.

FIGS. 5 and 6 illustrate schematic views of a self-checkout vending apparatus in accordance with a first embodiment of the present invention, which features a sliding door. The self-checkout vending apparatus automatically calculates the value of the unpackaged products based on a weighing by difference method. The numbered labels in the FIGS. 5-6 indicate different parts of the apparatus: 1001—Display; 1002—Code scan area; 1003—End button; 1004—Sliding door; 1005—Slider; 1006—Fitting component; 1007—Protective shield; 1008—Control panel; 1009—Base unit; 1010—Nut; 1011—Nut mount; 1012—Screw rod; 1013—Linear guide; 1014—Electric motor; 1015—Fitting for electric motor; 1016—Holder; 1017—Product tray.

FIGS. 7-10 illustrate schematic views of a self-checkout vending apparatus in accordance with a second embodiment of the present invention, which features a roll top cover. The self-checkout vending apparatus automatically calculates the value of the unpackaged products based on a weighing by difference method. The numbered labels in the FIGS. 7-10 indicate different parts of the apparatus: 2001—Fixed cover; 2002—Roll top cover; 2003—Transmission gear; 2004—Bearing; 2005—Motor gear; 2006—Electric motor; 2007—Base unit; 2008—Display; 2009—Code scan area; 2010—Reset button; 2011—Fitting component; 2012—Product tray; 2013—Control Panel.

Other than the door/cover moving mechanism, the first embodiment and the second embodiment of self-checkout vending apparatuses share a similar functional structure. As illustrated in the block diagram FIG. 11, the first/second self-checkout vending apparatus for unpackaged products comprises a central processing unit 7020, a product tray 7002, load cells 7003, a power supply 7010, a keypad interface 7040, a keypad 7041, a display interface 7050, a display 7051, a controller 7030 for sliding door or roll top cover, a motor driver 7032, an electric motor 7033, data storage 7026, transceiver 7025, and communication module 7024. The product tray 7002 is corresponding to the product tray 1017 in FIGS. 5-6 for the first embodiment, or the product tray 2012 in FIGS. 7-10 for the second embodiment. In a further preferred embodiment, the vending apparatus works with a cloud-based server 7100, which may control the vending apparatus off-site.

Figure 12:
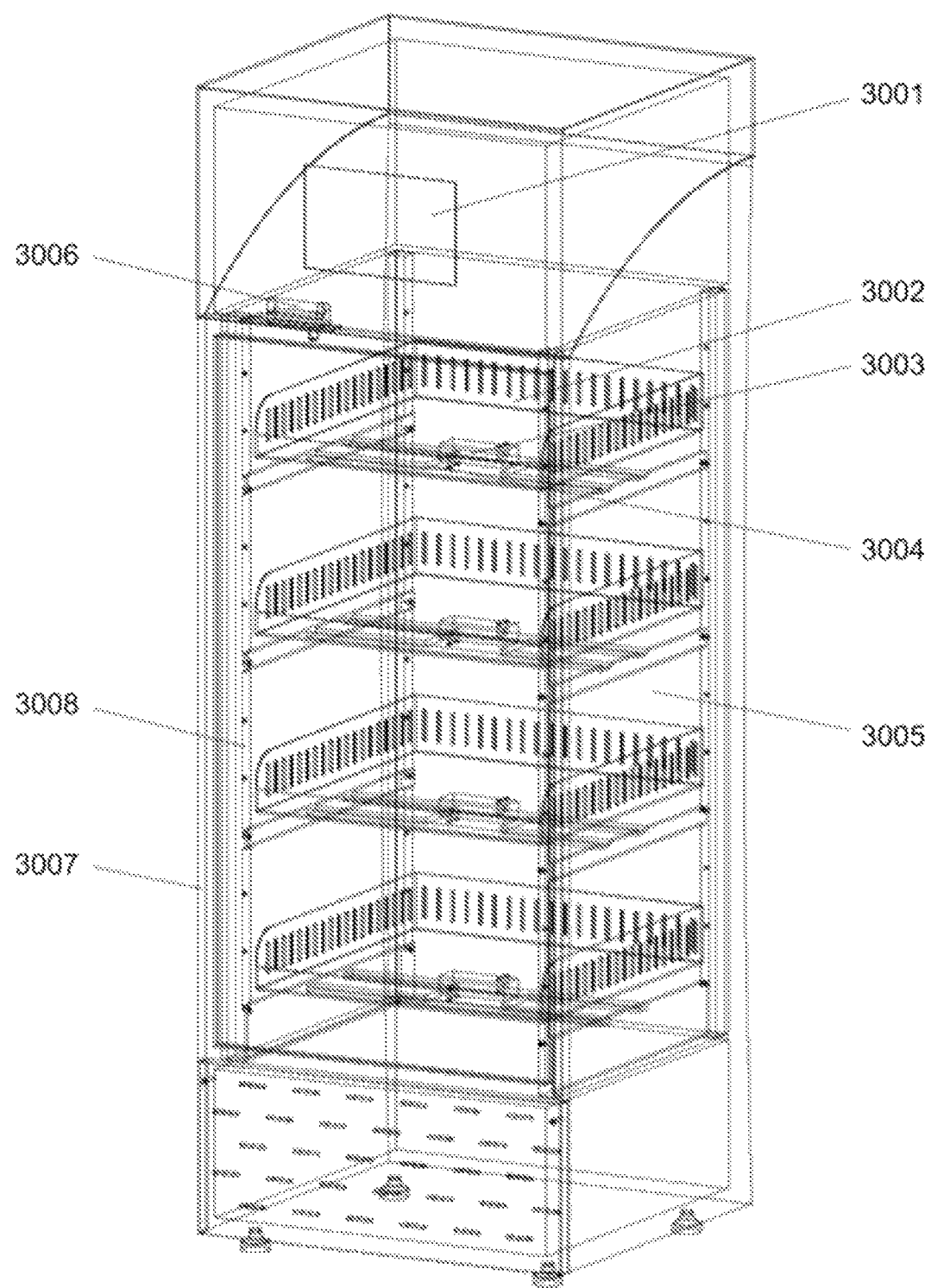
FIG. 12 illustrates the schematic view of a weight-based self-checkout vending apparatus in accordance with a third embodiment of the present invention.

FIG. 12 illustrates a schematic view of a self-checkout vending apparatus in accordance with a third embodiment of the present invention, which features a cabinet that displays products on a plurality of product trays. The numbered labels in the FIG. 12 indicate different parts of the apparatus: 3001—Display unit; 3002—Product tray; 3003—Load cells; 3004—Shelf; 3005—Cabinet; 3006—Electromagnetic lock; 3007—Cabinet door; 3008—Rack.

Figure 13:
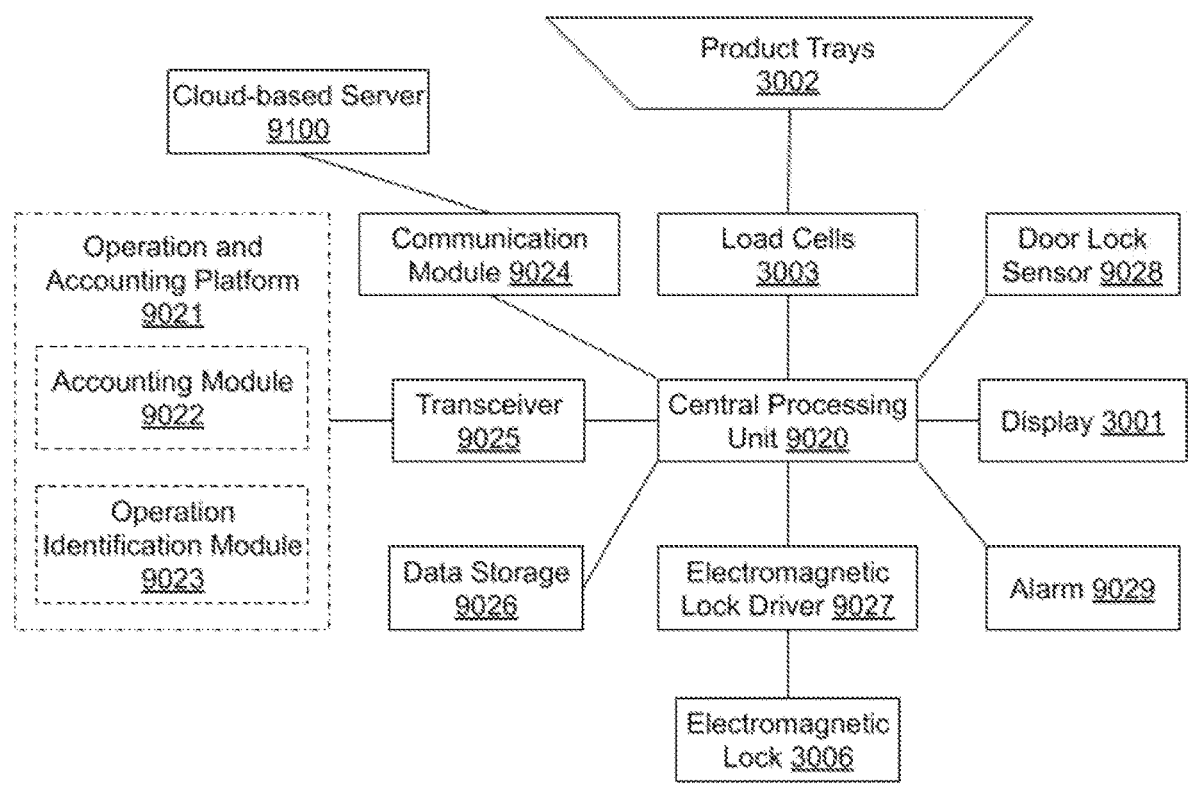
FIG. 13 depicts a block diagram of a weight-based self-checkout vending system including major functional blocks of a self-checkout vending apparatus in accordance with the third embodiment of the present invention.

FIG. 13 illustrates a block diagram of a self-checkout vending system including major functional blocks of the self-checkout vending apparatus in accordance with the third embodiment of the present invention. As illustrated, the system of FIG. 13 is similar to the system of FIG. 11 other than the product access control mechanisms and their relevant functions: Electromagnetic Lock 3006, Electromagnetic Lock Driver 9027, and Door Lock Senor 9028 in FIG. 13 vs. Controller for Sliding Door or Roll Top Cover 7030, Motor Driver 7032, Motor 7033, and Reset/Complete Button 7031 in FIG. 11.

E1. Detailed Description of the First Embodiment

Figure 11:
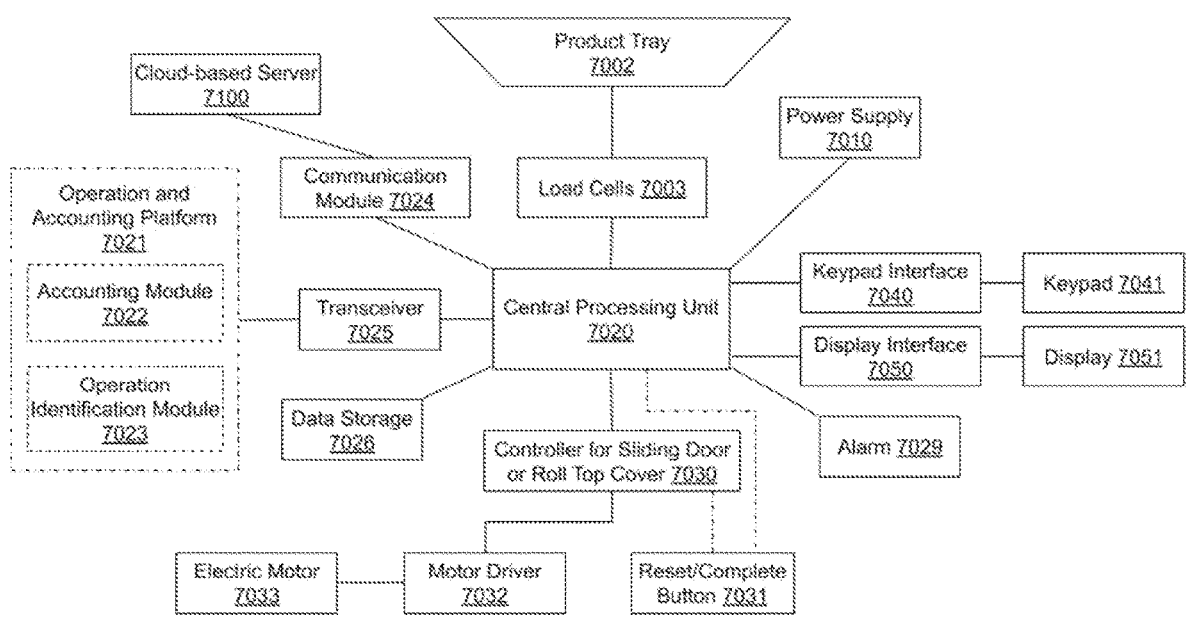
FIG. 11 depicts a block diagram of a weight-based self-checkout vending system including major functional blocks of a self-checkout vending apparatus in accordance with the first embodiment and the second embodiment of the present invention.

As illustrated in FIGS. 5, 6, and 11, a first embodiment of self-checkout vending apparatus is based on a weighing by difference method for selling unpackaged products. The apparatus comprises a display 1001, a keypad 7041, an alarm 7029, an end button 1003, a sliding door 1004, a slider 1005, a fitting component 1006, a protective shield 1007, a control panel 1008, a base unit 1009, a nut 1010, a nut mount 1011, a screw rod 1012, a linear guide 1013, an electric motor 1014, a fitting for the electric motor 1015, a holder 1016, a product tray 1017, and a controller unit. As illustrated in FIG. 11, the controller unit further comprises load cells 7003, a central processing unit 7020, a power supply 7010, a keypad interface 7040, a display interface 7050, a sliding door controller 7030 (optional), a motor driver 7032, a data storage 7026, a transceiver 7025, and a communication module 7024. The present invention may further comprise a cloud-based server 7100 that controls the self-checkout vending apparatus remotely.

As illustrated in FIGS. 5, 6, and 11, the control panel 1008 is on top of the base unit 1009. In a preferred embodiment, the control panel 1008 is made of glass. The base unit 1009 has a rectangular opening on the top, where the product tray 1017 is placed. The product tray 1017 is used for holding a given amount of goods, which is a type of product, especially unpackaged product, that is offered for sale. A weight sensor such as one or more load cells 7003 is under the product tray 1017. The load cells 7003 is connected to a central processing unit 7020. The load cells 7003 measures the current weight of the remaining goods on the product tray 1017 and updates the central processor 7020 about the weight in real time. When the central processor 7020 receives a completion signal, the central processor 7020 calculates an amount of goods taken by a customer (i.e., weight of goods sold) based on the difference between an initial weight from the load cells 7003 and the current remaining goods weight from the load cells 7003. The completion signal indicates that the customer has finished taking the goods on the product tray 1017. Next, the central processor 7020 calculates a cost of goods taken by the customer (i.e., payment amount) based on the weight of goods sold and a unit price of goods (i.e., the unit price for the type of product for sale). The unit price is stored in a data storage 7026.

The product tray 1017 is surrounded by a fitting component 1006. The fitting component is securely mounted on the base unit 1009 and forms a rectangular surrounding structure outside of the product tray 1017. The protective shield 1007 can be then fastened onto the base unit 1009 by attaching it to the inner surface or the outer surface of the fitting component 1006. The means of fastening may be using glue, recessed grooves, or screws, etc. The protective shield 1007 protects the goods offered for sale on the product tray 1017. Preferably the protective shield 1007 is transparent so that the customers can clearly view the product inside. On at least one side of the protective shield 1007, there is an opening through which the goods can be placed and taken. The sliding door 1004 conforms to the shape of the opening. The preferred shape of the opening is rectangular. The sliding door can be moved to facilitate the placing and fetching the goods inside. The opening of the protective shield 1007 serves as the product access window.

An actuator for the sliding door is mounted in a corner of the protective shield close to the product access window. The actuator is fastened onto the inner surface of the fitting component 1006. The actuator comprises a slider 1005, a nut 1010, a nut mount 1011, a screw rod 1012, a linear guide 1013, an electric motor 1014 for moving the sliding door, a fitting for the electric motor 1015, and a holder 1016. The holder 1016 is fastened to an inner surface of the base unit 1006 near the product access window. The fitting for the electric motor 1015 is fastened to the top of the holder 1016. The electric motor 1014 is mounted on the ceiling of the fitting for the electric motor 1015. The screw rod 1012 is installed under the fitting for the electric motor 1015. The screw rod 1012 extends vertically along the linear guide 1013. The rotation of the screw rod 1012 is driven by its top attached to the output shaft of the electric motor 1014. The slider 1005 is connected to the screw rod 1012 and can move up and down along it. One side of the sliding door 1004 is fastened to the slider 1005. More specifically, the slider 1005 is mounted to the sliding door 1004 through the nut 1010 and the nut mount 1011. In this way, the electric motor 1014 drives the screw rod to rotate, which moves the slider 1005 up and down, and in turn moves the sliding door 1004 up and down. Hence the sliding door 1004 can control the opening and close of the product access window. When the sliding door 1004 is driven by the slider 1005 to move upwards, the product access window is opened. When the sliding door 1004 is driven by the slider to move downwards, the window is then closed.

The control panel 1008 further comprises a display 1001, a code scan area 1002, and an end button 1003, which are preferably in the front of the sliding door. The display 1001 (i.e., 7051 in FIG. 11) is connected to the central processing unit 7020 via the display interface 7050. The central processing unit 7020 displays customer's purchasing and payment information on the display 1001 in real time. The code scan area 1002 has a scannable code, which is preferably a 2D barcode or QR code that supports WeChat payment and Alipay. The end button 1003 is connected to either the central processing unit 7020 or a sliding door controller 7030.

In a further preferred embodiment, the sliding door 1004 may be made of glass or acrylic glass. The protective shield is fixed glass shield. The control panel is also made of glass. The screw rod is preferred to be a ball screw rod. The electric motor is preferred to be a stepper motor, which transforms the rotation to linear movement via the ball screw rod.

A controller unit is installed inside the base unit 1009. The controller unit comprises load cells 7003, a central processing unit 7020, a power supply 7010, a keypad interface 7040, a display interface 7050, a motor driver 7032, a data storage 7026, a transceiver 7025, and a communication module 7024. The central processing unit 7020 is preferably an ARM 32-bit central processor. The central processing unit 7020 is connected to the load cells 7003, the power supply 7010, the keypad interface 7040, the display interface 7050, the alarm 7029, the data storage 7026, the transceiver 7025, and the commination module 7024.

The load cells 7003 detect a current weight of product on the product tray 1017 and sends a measurement to the central processing unit 7020 in real time. Hence the central processing unit 7020 has an initial weight of the goods on the product tray 1017 before a customer starts taking some of the goods from the vending apparatus. After the customer finishes taking the desired amount of the goods from the vending apparatus, the central processing unit 7020 receives a completion signal and then automatically calculates and displays a cost of the goods taken by the customer based on the following: a most updated weight of the remaining goods on the product tray 1017, a weight difference between the initial weight stored in the data storage and the updated weight, and the unit price of the goods stored in the data storage. The central processing unit 7020 generates an amount due based on the cost of goods taken by the customer. Finally, the central processing unit 7020 shows the amount due on the display 1001 to the customer and sends the amount due to an operation and accounting platform 7021 to close the transaction.

The data storage 7026 connected to the central processing unit 7020 stores the unit price of the goods offered for sale and the initial weights of the goods prior to each transaction. The unit price is received during an initialization when the vending apparatus is replenished with the goods for sale. The central processing unit 7020 controls the data storage 7026 that maintains the initial weight. The central processing unit 7020 updates the current initial weight using the most recently received weight of the remaining goods on the product tray 1001 after a purchase. The data storage 7026 also stores other essential data information that is required for the central processing unit 7020 to perform its tasks. The essential data information may be initialized via data initialization or received from the cloud-based server 7100.

The keypad 7041 may be installed on the control panel 1008 or on the back of the base unit 1009. Keypad operation signals are passed to the central processing unit 7020 via the keypad interface 7040.

When detecting abnormal activities, the central processing unit 7020 controls the alarm 7029 to generate alerts. The central processing unit 7020 may also be linked to a cloud-based server 7100 via the communication module 7024, hence enabling a remote control or off-site control of the self-checkout vending apparatus.

The sliding door controller 7030 may be integrated into the central processing unit 7020 as a function of the central processing unit. Alternatively, the controller 7030 is implemented separately. The controller 7030 is connected to the central processing unit 7020 and the motor driver 7032 which is connected to the motor 7033. A control signal from the central processing unit 7020 is processed by the sliding door controller 7030 and forwarded to the motor driver 7032, which then drives the motor 7033 to rotate, which then opens or closes the sliding door 1004 accordingly.

The end button 7031 (7031 in FIG. 11 or 1003 in FIG. 5) can be connected in two different methods. In the first method, the end button 7031 is connected to the sliding door controller 7030. When a customer finishes getting goods, the customer presses the end button 7031, hence sending a completion signal to the sliding door controller 7030. The sliding door controller 7030 signals the motor driver 7032 to close the sliding door 1004, and at the same time passes the completion signal to the central processing unit 7020. Upon receiving the completion signal, the central processing unit 7020 calculates the amount due and sends the amount due to the operation and accounting platform via the transceiver 7025.

In the second method, the end button 7031 is connected directly to the central processing unit 7020. When a customer finishes getting goods, the customer presses the end button 7031, hence sending a completion signal to the central processing unit 7020. Upon receiving the completion signal, the central processing unit 7020 calculates the amount due and sends the amount due to the operation and accounting platform via the transceiver 7025. At the same time, the central processing unit 7020 forwards the completion signal to the sliding door controller 7030. The sliding door controller 7030 signals the motor driver 7032 to close the sliding door 1004.

The present invention further comprises an operation and accounting platform 7021, which is wirelessly connected to the self-checkout vending apparatus. The self-checkout vending apparatus has a QR code or a QR code reader and can communicate with the operation and accounting platform 7021 via a scan of the QR code or the QR code reader. The operation and accounting platform 7021 comprises the accounting module 7022 and the operation identification module 7023. The operation identification module 7023 can communicate with user devices, such as mobile phones, and carry out user identification. The accounting module 7022 is responsible for communicating with the remote payment and accounting terminal (for example, WeChat and Alipay). The operation and accounting platform is wirelessly connected via the transceiver 7025. Preferably the transceiver 7025 is a wireless LAN transceiver and connects the central processing unit 7020 for external data communication.

When a customer using a mobile phone to scan the QR code or be scanned by the QR code reader, the operation identification module 7023 identifies the information scanned and sends confirmation information to the transceiver 7025. The transceiver passes the confirmation information to the central processing unit 7020, which in turn generates a control signal to open the sliding door 1004 to allow the customer to access the goods offered by the self-checkout vending apparatus. When the central processing unit 7020 generates a making payment signal and sends it to the remote accounting module 7022 via the transceiver 7025, the remote accounting module 7022 directly charges the payment amount to the customer account using a password-less authentication, or auto-debit service. Alternatively, the remote accounting module 7022 sends the payment information to the customer's mobile phone and allows the customer completes the transaction according to the payment information received. Finally, the remote accounting module 7022 sends the payment completion information to the central processing unit 7020 via the transceiver 7025. The payment completion information is to be stored in the data storage 7026.

In a further preferred embodiment, the self-checkout vending apparatus comprises a card reader embedded in the code scan area to support the conventional card payment means (for example, paying with debit/credit cards). Said card reader may be connected to the transceiver 7025. The automatic control of the sliding door 1004 may be based on signals from the car reader. And the payment transactions may be through the card reader.

An exemplary operating procedure of a self-checkout vending apparatus in accordance with the present invention is as follows.

A type of goods has been placed on the product tray of the self-checkout vending apparatus.

When a customer wants to buy the goods, he/she scans the QR code or uses the QR code reader on the self-checkout vending apparatus with a mobile phone.

The scanning activity triggers a request for access to goods is sent to the central processing unit. The central processing unit checks if the self-checkout vending apparatus is out of stock by measuring the current weight on the product tray. An out-of-stock alert will be triggered and transmitted by the central processing unit if the weight measured is zero. Otherwise, after a successful scan, the transceiver receives a scan confirmation information and provides an open access request information to the central processing unit. The central processing unit generates a signal to the sliding door controller based on the open access request information, and in turn open the sliding door via the electric motor. Therefore, it enables the customer to take the desired amount of goods.

When customers are taking goods from the product tray, the load cells continuously measure the current weight on the product tray and sends the real-time data to the central processing unit. The customers may press an end button when finishing getting the goods, which will notify the central processing unit to close the product access window and calculate the final weight of the goods sold by finding the difference between the weight on the scale before and after the transaction. The amount due is then computed by multiplying the weight of the goods sold and the unit price of the goods and then is displayed to customers. The central processing unit will generate payment information and send it to the remote accounting module, which then carries out a password-less authentication, or auto-debit service, or display the payment information at the customer's mobile phone to complete the payment transaction. Finally, the central processing unit retracts the sliding door and closes the product access window and completes the whole vending process.

E2. Detailed Description of the Second Embodiment

As illustrated in FIGS. 7-11, a second embodiment of self-checkout vending apparatus is based on a weighing by difference method for selling any products. The apparatus comprises a display 2008 (i.e., 7051 in FIG. 11), a keypad 7041, an alarm 7029, a fixed cover 2001, a roll top cover 2002, a transmission gear 2003, a bearing 2004, a motor gear 2005, an electric motor 2006, a base unit 2007, a fitting component 2011, a product tray 2012, a control panel 2013, and a controller unit. As illustrated in FIG. 11, the controller unit further comprises load cells 7003, a central processing unit 7020, a power supply 7010, a keypad interface 7040, a display interface 7050, a roll top cover controller 7030 (optional), a motor driver 7032, a data storage 7026, a transceiver 7025, and a communication module 7024. The present invention may further comprise a cloud-based server 7100 that controls the self-checkout vending apparatus remotely.

The self-checkout vending apparatus is equipped with QR code or QR code reader for making payments. User scanning the QR code or QR code reader scanning a user app code generates a request for getting goods to the central processing unit 7020. A reset button 2010 is mounted on the base unit 2007 and connected to the central processing unit. Pressing the reset button 2010 after collecting the desired amount will trigger a completion signal to the central processing unit 7020.

The central processing unit 7020 first determines if the vending apparatus is in stock after receiving the request. Specifically, the central processing unit 7020 reads the measurement by the load cell 7003 and checks if the detected weight on the product tray 2012 is zero. If it is, the vending apparatus is determined to be out of stock and the central processing unit displays an out-of-stock message; otherwise, the central processing unit drives an actuator to roll up the top cover.

As illustrated in FIGS. 7-11, the control panel 2013 is on top of the base unit 2007. In a preferred embodiment, the control panel 2013 is made of fine-quality glass. The base unit 2007 has a rectangular opening on the top, where the product tray 2012 is placed. The product tray 2012 is used for placing a given amount of goods, which are a type of product, especially unpackaged product, that is offered for sale. One or more load cells 7003 are under the product tray 2012. The load cells 7003 are connected to a central processing unit 7020. The load cells 7003 measure the current weight of the remaining goods on the product tray 2012 and updates the central processor 7020 about the weight in real time. When the central processor 7020 receives a completion signal, the central processor 7020 calculates an amount of goods taken by a customer (i.e., weight of goods sold) based on the difference between an initial goods weight from the load cells 7003 and the current remaining goods weight from the load cells 7003. The completion signal indicates that the customer has finished taking the goods from the product tray 2012. Next, the central processor 7020 calculates a cost of the goods taken by the customer (i.e., payment amount) based on the weight of goods sold and a unit price of goods (i.e., the unit price for the type of product for sale). The unit price is stored in a data storage 7026. The unit price is initialized when the self-checkout vending apparatus is furnished with the goods for sale. The data storage 7026 also stores the initial goods weight before the customer takes goods. The initial goods weight is updated by the current remaining goods weight each time after a sales transaction from the self-checkout vending apparatus is ended.

Figure 9:
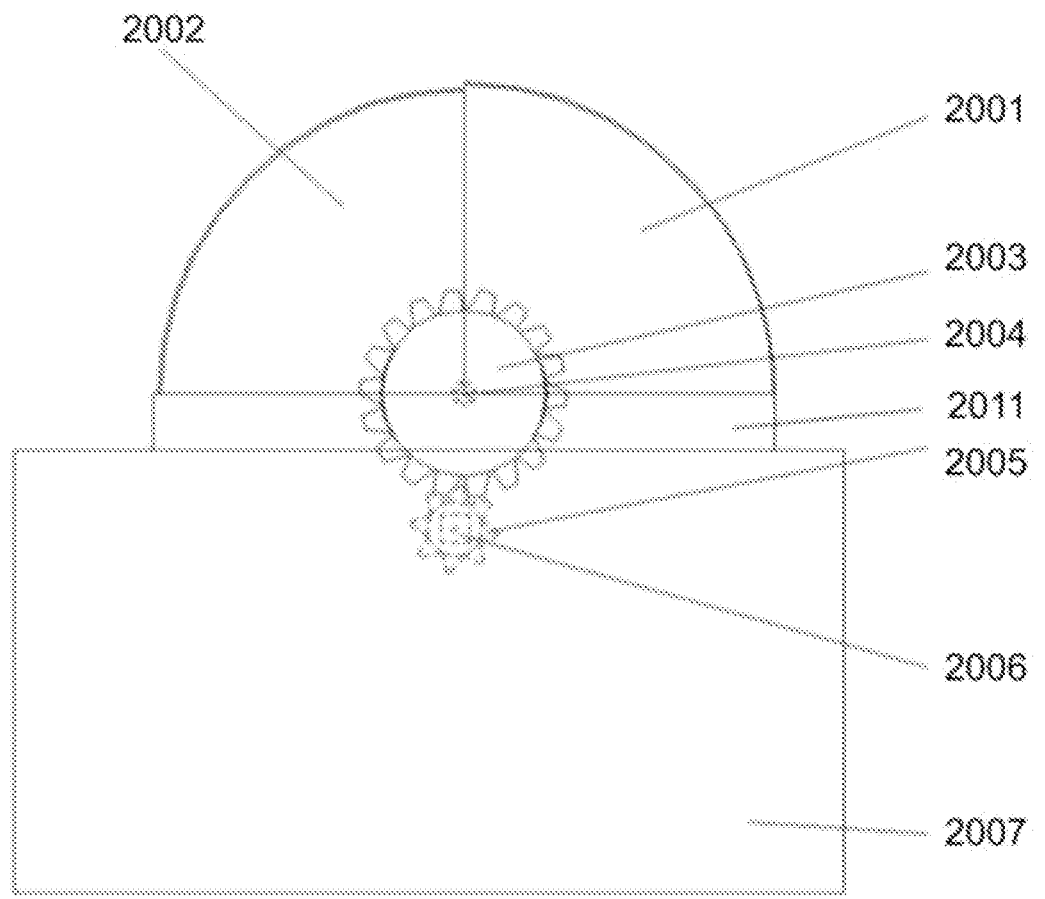
FIG. 9 illustrates the end view of the weight-based self-checkout vending apparatus in accordance with the second embodiment of the present invention.
Figure 10:
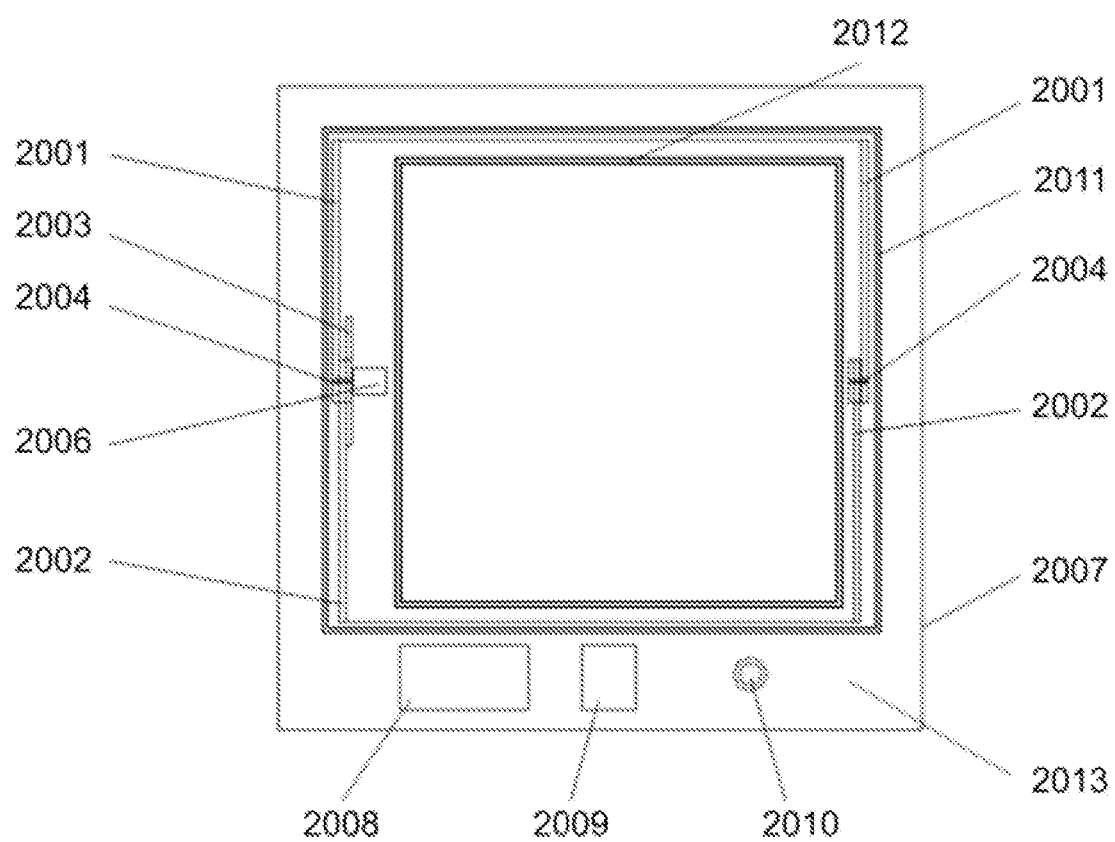
FIG. 10 illustrates the top view of the weight-based self-checkout vending apparatus in accordance with the second embodiment of the present invention.

The product tray 2012 is surrounded by a fitting component 2011. The fitting component is securely mounted on the base unit 2007 and forms a rectangular surrounding structure outside of the product tray 2012. The fixed cover 2001 is fastened onto the base unit 2007 by attaching it to the inner surface of the fitting component 2011. The fixed cover 2001 is preferably made of transparent curved glass, allowing customers to clearly see the goods on the product tray 2012. The fixed cover 2001 has a front, a back, and two ends. As shown in FIG. 9, the ends of the fixed cover 2001 are roughly a quarter circle shaped. The fixed cover 2001 is in the shape of a quarter cylinder. The bottom part of the fixed cover 2001 may be fastened onto the fitting component 2011 using glue, recessed grooves, screws, or other methods. The roll top cover 2002 has a shape that is consistent with the fixed cover 2001. The roll top cover 2002 also has a front, a back, and two ends, and is of the same shape as the fixed cover 2001. The diameter of the roll top cover is slightly smaller than that of the fixed cover 2001. The side of the roll top cover has a slightly smaller O.D (i.e., outside diameter) than the I.D. (inner diameter) of the side of the fixed cover 2001 and it is also shorter. Both sides are of same thickness. The roll top cover 2002 can be rolled up and be completely housed inside of the fixed cover 2001. The opening of the fixed cover 2001 faces to the control panel 2013. The fixed cover 2001 together with the roll top cover 2002 when closed fully encloses the product tray 2012 and the goods on it. When the roll top cover 2002 is rolled up, it opens a product access window for customers to get the goods on the product tray 2012.

Figure 7:
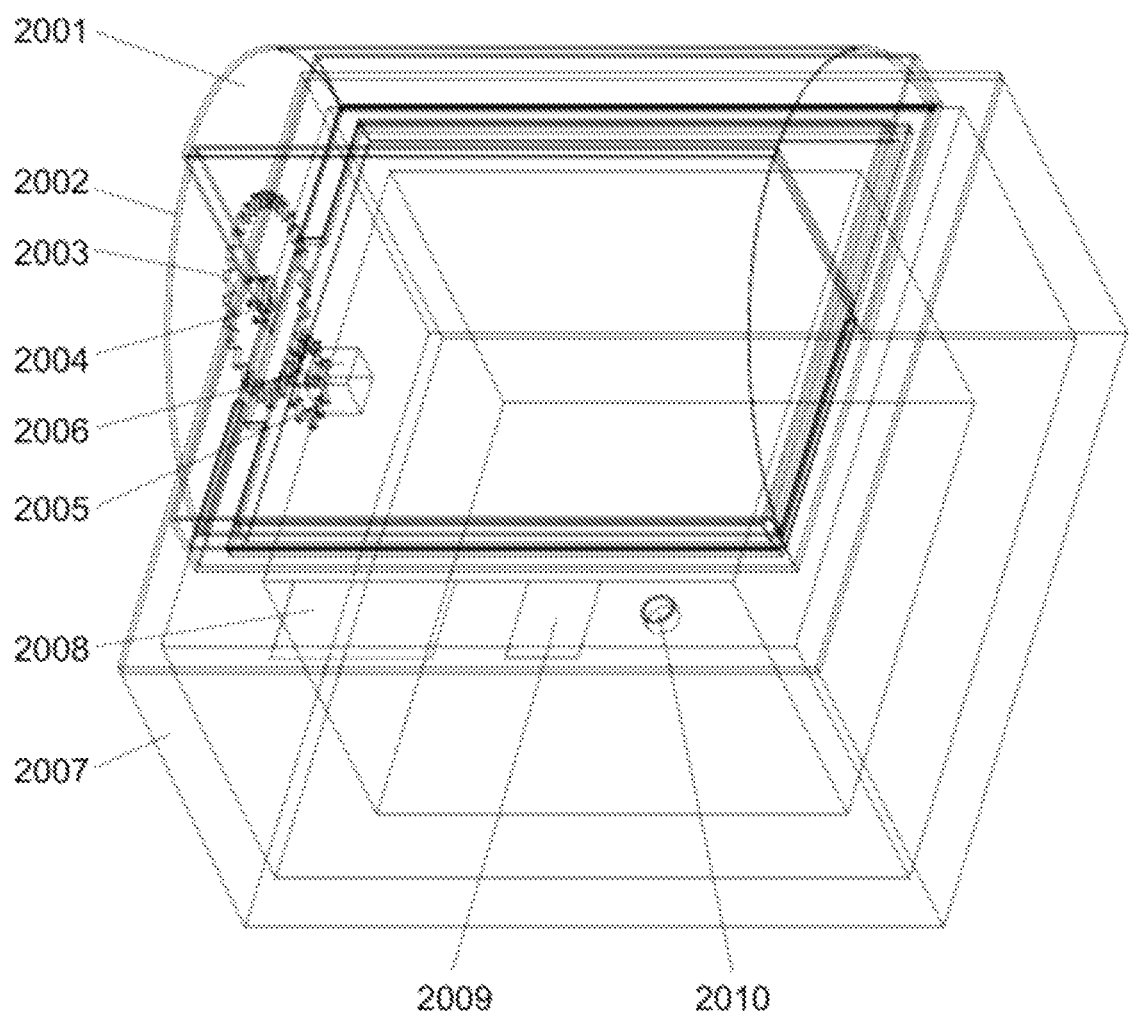
FIG. 7 illustrates a schematic view of a weight-based self-checkout vending apparatus in accordance with a second embodiment of the present invention.
Figure 8:
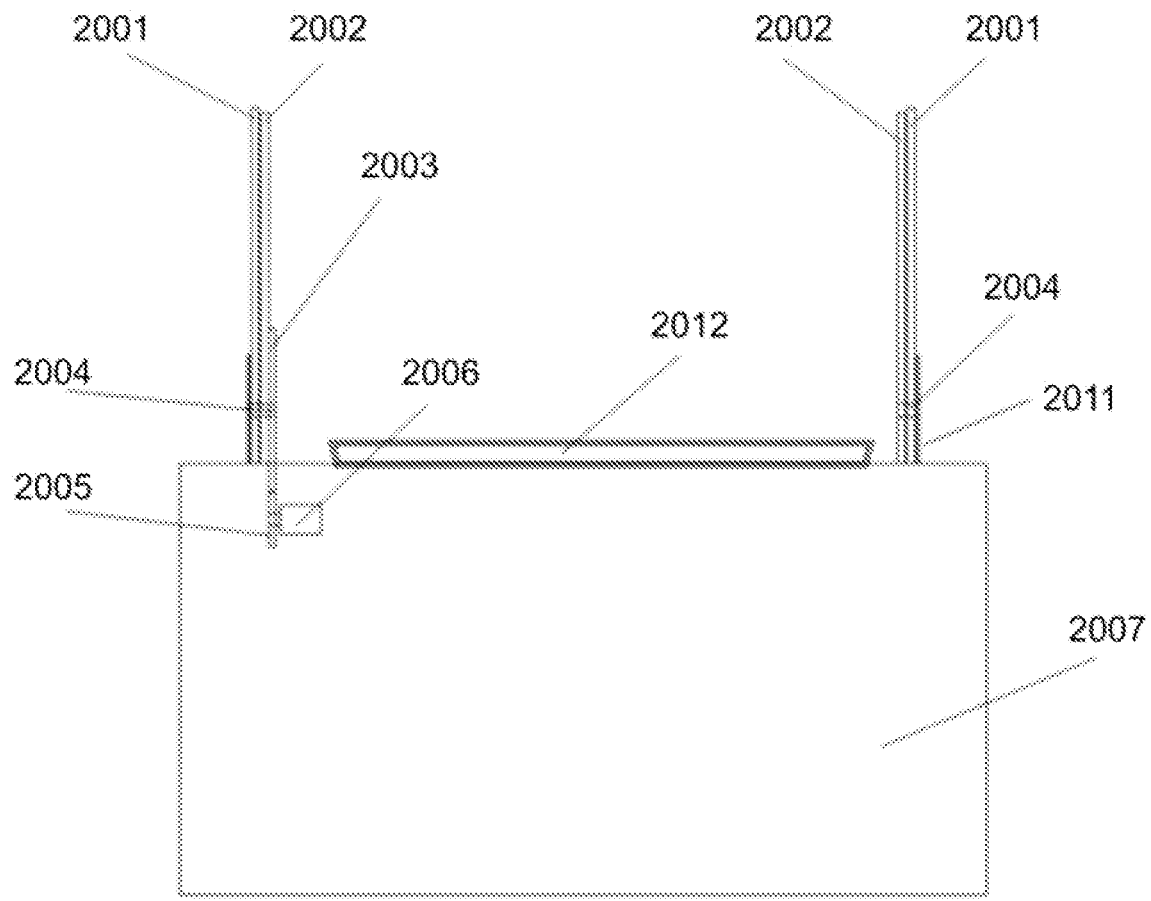
FIG. 8 illustrates the front view of the weight-based self-checkout vending apparatus in accordance with the second embodiment of the present invention.

The fitting component 2011 may have a groove surrounding the bottom of the inner surface that match the edges of the roll top cover. In this way, the roll top cover when closed is sitting on the fitting component 2011. To open and close the product access window, the self-checkout vending unit may further comprise an actuator to control the roll top cover 2002. The actuator is connected to the roll top cover 2002 and can drive the top cover 2002 to rotate along the inner surface of the fixed cover 2001 until it is fully housed or fully returned. When the roll top cover 2002 is completely housed by the fixed cover 2001, the product access window is opened. When the roll top cover is returned to its initial position, the product access window is closed. As illustrated in FIG. 7, the actuator comprises a transmission gear 2003, a bearing 2004, a motor gear 2005, an electric motor 2006 and its driver. The transmission gear 2003 is attached to the inner surface of one end of the roll top cover. The transmission gear 2003 is fastened on one end of the roll top cover 2002. In an alternative implementation, both ends of the roll top cover may be equipped with synchronized transmission gears, depending on the strength of actuation. The center of the transmission gear 2003 is attached to the fitting component 2011 via the bearing 2004. The bearing 2004, supporting the rotation of the transmission gear 2003 and the roll top cover 2002, comprises 2 ball bearings that are set up collinearly. The ball bearings are attached to the two sides of the fitting component 2011 through the holes located near the corner of the roll top cover 2002. The bearing 2004 is mounted to the transmission gear 2003 that is fastened on the inner surface of one end of the roll top cover 2002. The roll top cover 2002 may be partially overlapped by the fixed cover 2001. On the fixed cover 2001 and the roll top cover 2002, the holes through which the ball bearings are mounted to both ends of the fitting component 2011 are also in the same position. This allows the transmission gear 2003 to rotate freely around the fixed axis of the bearing 2004. The rotation of the transmission gear 2003 may then engage the rotation of the attached roll top cover 2002. The transmission gear 2003 is engaged with the motor gear 2005, which is positioned within the base unit 2007. The center of the transmission gear 2005 is connected to the output shaft of the motor 2006. The motor 2006 is mounted within the base unit 2007 and is connected to the motor driver. When the motor driver 7032 is instructed by the central processing unit 7020 to open the product access window, the motor 2006 turns on and the movement of its output shaft engages the rotation of the motor gear 2003, which engages the rotation of the transmission gear 2003 and the top cover attached to it. The top cover 2002 is being rolled towards the fixed cover 2001 until being fully housed. This opens the product access window and allows a customer to take a desired amount of goods. When the customer finishes, the central processing unit 7020 signals the motor driver 7032 to close the product access window. The motor drive 7032 re-starts the motor 2006, whose output shaft drives the motor gear 2005 to rotate reversely, engaging the rotation of the transmission gear 2003 and the top cover 2002 that is attached to it. The top cover 2002 is being retracted away from the fixed cover 2001 until it fully covers the product tray 2012 together with the fixed cover 2001. The movements of the transmission gear 2003, the motor gear 2005, the motor 2006 and the bearing 2004 do not interfere the product tray 2012.

The control panel 2013 further comprises a display 2008, a code scan area 2009, and a reset button 2010, which are preferably in the front of the roll top cover 2002. The display 2008 (i.e., 7051 in FIG. 11) is connected to the central processing unit 7020 via the display interface 7050. The central processing unit 7020 displays customer's purchasing and payment information on the display 2008 in real time. The code scan area 2009 has a QR code that supports payments via WeChat and payments via Alipay. Alternatively, the code scan area 2009 may have a code reader that supports WeChat payment and Alipay. The reset button 2010 is connected to either the central processing unit 7020 or the roll top cover controller 7030. The fixed cover 2001 and the roll top cover 2002 are preferably made of fine-quality transparent glass. The control panel 2013 is preferably made of fine-quality glass.

A controller unit is inside the base unit 2007. The controller unit comprises load cells 7003, a central processing unit 7020, a power supply 7010, a keypad interface 7040, a display interface 7050, a motor driver 7032, a data storage 7026, a transceiver 7025, and a communication module 7024. The central processing unit 7020 is preferably an ARM 32-bit central processor. The central processing unit 7020 is connected to the load cells 7003, the power supply 7010, the keypad interface 7040, the display interface 7050, the alarm 7029, the data storage 7026, the transceiver 7025, and the commination module 7024.

The load cells 7003 detect a current weight of remaining goods on the product tray 2012 and sends a measurement to the central processing unit 7020 in real time. Hence the central processing unit 7020 has an initial weight of the goods on the product tray 2012 before a customer starts taking some goods from the vending apparatus. After the customer finishes taking the desired amount of goods from the vending apparatus, the central processing unit 7020 receives a completion signal and then automatically calculates and displays a cost of goods taken by the customer based on the following: the most updated weight of remaining goods on the product tray 2012, a weight difference between the initial weight stored in the data storage and the most updated weight, and the unit price of the goods stored in the data storage. The central processing unit 7020 generates an amount due based on the cost of goods taken by the customer. Finally, the central processing unit 7020 shows the amount due on the display 2008 to the customer and sends the amount due to an operation and accounting platform 7021 to close the transaction.

The data storage 7026 connected to the central processing unit 7020 stores the unit price of the goods offered for sale and the initial weights of the goods prior to each transaction. The unit price is received during an initialization when the vending apparatus is replenished with the goods for sale. The initial weights are obtained from the weights of the remaining goods on the product tray 2008 after each transaction. The central processing unit 7020 updates the current initial weight using the current weight of the remaining goods on the product tray 2008 after each time generating the amount due for payment. The data storage 7026 also stores other essential data information that is required for the central processing unit 7020 to perform its tasks. The essential data information may be initialized via data initialization or received from the cloud-based server 7100.

When detecting anomalies, the central processing unit 7020 controls the alarm 7029 to produce alerts. The central processing unit 7020 may be linked to a cloud-based server 7100 via the communication module 7024 for remote operation and monitoring of the vending unit. The information stored in the data storage 7026 may also be entered via the cloud-based server 7100.

The keypad 7041 is mounted on the back panel of the base unit and sends corresponding keypad operation information to the central processing unit 7020.

The roll top cover controller 7030 may be integrated into the central processing unit 7020 (that is, the controlling functions are added to the central processing unit). Alternatively, the controller 7030 is implemented separately. The controller 7030 is connected to the central processing unit 7020 and the motor driver 7032 which is connected to the motor 7033. A control signal from the central processing unit 7020 is processed by the top cover controller 7030 and forwarded to the motor driver 7032, which then drives the motor 7033 to rotate.

The reset button 7031 (7031 in FIG. 11 or 2010 in FIGS. 7 and 10) can be connected in two different methods. In the first method, the reset button 7031 is connected to the roll top cover controller 7030. When a customer finishes getting goods, the customer presses the reset button 7031, hence sending a completion signal to the roll top cover controller 7030. The roll top cover controller 7030 signals the motor driver 7032 to close the roll top cover 2002, and at the same time passes the completion signal to the central processing unit 7020. Upon receiving the completion signal, the central processing unit 7020 calculates the amount due and sends the amount due to the operation and accounting platform via the transceiver 7025 to settle the payment transaction.

In the second method, the reset button 7031 is connected directly to the central processing unit 7020. When a customer finishes getting goods, the customer presses the reset button 7031, hence sending a completion signal to the central processing unit 7020. Upon receiving the completion signal, the central processing unit 7020 calculates the amount due and sends the amount due to the operation and accounting platform via the transceiver 7025. At the same time, the central processing unit 7020 forwards the completion signal to the roll top cover controller 7030. The roll top cover controller 7030 signals the motor driver 7032 to close the roll top cover 2002.

The present invention further comprises an operation and accounting platform 7021, which is wirelessly connected to the self-checkout vending apparatus. The self-checkout vending apparatus may be equipped with a QR code or a QR code reader and can communicate with the operation and accounting platform 7021 via the scan of the QR code or the QR code reader. The operation and accounting platform 7021 comprises the accounting module 7022 and the operation identification module 7023. The operation identification module 7023 can communicate with a consumer device, such as a mobile phone, and carry out consumer identification. The accounting module 7022 may be a remote payment terminal, such as a WeChat or Alipay service terminal. The operation and accounting platform is wirelessly connected via the transceiver 7025. Preferably the transceiver 7025 is a wireless LAN transceiver and connects the central processing unit 7020 for external data communication.

When the QR code or the QR code reader is scanned by the consumer, the operation and accounting platform 7021 confirms the consumer's identification and sends confirmation information to the transceiver 7025, which then requests for opening the product access window to the central processing unit 7020. The central processing unit 7020 then drives the roll top cover controller 7030 to roll the cover and open the product access window, which allows the consumer to get the goods on the product tray. The accounting signal generated by the central processing unit 7020 is sent to the remote accounting module 7022, which settles the payment via password-less authentication or displays the payment information to the customer's mobile phone and allows the customer to complete the transaction according to the payment information received. The settled payment information is then fed to the transceiver 7025, which sends the information to the central processing unit 7020. The central processing unit 7020 then stores the payment information.

In a further preferred embodiment, the self-checkout vending apparatus comprises a card reader on the control panel 2013 to support the conventional card payment means (i.e., paying with debit/credit cards). The card reader may be connected to the transceiver 7025. The automatic control of the roll top cover 2002 may be based on signals from the car reader.

A brief exemplary operating procedure of a self-checkout vending apparatus in accordance with the second embodiment of the present invention is as follows.

First, goods to be sold are placed on the product tray of the self-checkout vending apparatus.

A customer may scan the QR code or use the QR code reader on the self-checkout vending apparatus. The scanning activity is confirmed by the operation identification module. The confirmation information is received by the transceiver, which then passes the request for opening the product access window to the central processing unit. The central processing unit then drives the roll top cover controller to rotate the motor and open the roll top cover to open the product access window. While the customer is getting goods, the load cell measures the current weight of goods on the product tray and sends its measurement to the central processing unit. The customer may press the reset button when finishing getting goods, which triggers the signal that closes the product access window. The motor then rotates reversely, engaging a reverse rotation of the gear that retracts the roll top cover to close the product access window. Meanwhile, the reset button sends a completion signal to the central processing unit. The central processing unit calculates the weight of goods sold based on the difference between the weight on the product tray before the customer gets the goods and the weight on the product tray after the customer gets the goods. The central processing unit calculates the amount due by multiplying the weight of goods sold by the unit price of the goods. The payment information is then transmitted to the remote accounting terminal, which then settles the payment via password-less authentication accordingly. The remote accounting terminal then stores the payment information in the storage system, signaling the completion of this self-checkout.

E3. Detailed Description of the Third Embodiment

As illustrated in FIGS. 12 and 13, the present invention comprises a self-checkout vending apparatus which is based on a weighing by difference method and enables vending unpackaged products like cooked food, fruits, and vegetables. The vending apparatus may have a freezer, a refrigerator, or a fresh-keeping cabinet. The vending apparatus comprising a display unit 3001, product trays 3002, load cells 3003, shelves 3004, a cabinet body 3005, an electromagnetic lock 3006, a cabinet door 3007, a rack 3008, and a controller unit. The controller unit comprises a door lock sensor 9028, a central processing unit 9020, an electromagnetic lock driver 9027, a data storage 9026, a transceiver 9025, an alarm 9029, and a communication module 9024.

In FIG. 12, the cabinet 3005 has a multiple-tier shelving structure. As shown, a rack has four vertical parallel bars mounted at the cabinet inner corners. Each bar has a plurality of evenly spaced holes. The shelves 3004 comprises left beams, middle beams, and right beams. Each beam can be connected to the different positions on the rack using different holes. Each one of the middle beams of the shelves 3004 is equipped with the load cells 3003. Each product tray 3002 is placed on one of the shelves 3004 above the load cells 3003. The load cells 3003 detect a weight on each product tray 3002 in real time. The controller box is located on top of the cabinet 3005. The controller box contains the display unit 3001 and the controller unit. The display unit 3001 includes a monitor. The electromagnetic lock 3006 may be equipped between the cabinet frame and the cabinet door. The controller unit may be equipped in the controller box. The electromagnetic lock 3006, the load cells 3003, the display unit 3001 are connected to the controller unit. If the vending apparatus has a temperature control, a cooling unit that keeps the products fresh may be located at the bottom of the cabinet.

As illustrated in FIG. 13, the controller unit comprises the door lock sensor 9028, the central processing unit 9020, the electromagnetic lock driver 9027, the data storage 9026, the transceiver 9025, the alarm 9029, and the communication module 9024. The present invention may also include a cloud-based server that can remotely control the vending apparatus. The central processing unit 7020 is preferably the ARM 32-bit microcontroller. The load cells 3003 are connected to the central processing unit 7020 and update the central processing unit 7020 regarding the weight on each product tray in real time. Based on that, central processing unit 7020 determines a weight of goods sold based on the difference of the detected weights before and after a sale. The door lock sensor 9028 detects whether the door is closed and sends its detected door status to the central processing unit 7020.

The data storage 9026 is connected to the central processing unit 9020 and stores unit price information, initial weight information, and other information of the products for sale. More specifically, the unit price information and initial weight information of goods on each product tray are stored in the system, where the information can be indexed according to the IDs of the load cells beneath product trays. An exemplary format of the information records is illustrated in table 7 below:

TABLE 7

| Load cell ID1 of product tray 1 | Unit Price of goods on product tray 1 | Initial weight of goods on product tray 1 | . . . |
| --- | --- | --- | --- |

TABLE 7-continued

| Load cell ID2 of product tray 2 | Unit Price of goods on product tray 2 | Initial weight of goods on product tray 2 | ... |
| Load cell ID3 of product tray 3 | Unit Price of goods on product tray 3 | Initial weight of goods on product tray 3 | ... |
| ... | ... | ... | ... |

The IDs for load cells, the unit price information, and initial weight information for goods on each product tray are initialized via a remote server or the keypad after each replenishment. The initial weight information is updated by the central processing unit 9020 each time a purchase is completed. The above information records may also include the name of goods on each product tray as illustrated in table 8 below:

TABLE 8

| Load cell ID1 of product tray 1 | Unit Price of goods on product tray 1 | Name of goods on product tray 1 | Initial weight of goods on product tray 1 | ... |
| Load cell ID2 of product tray 2 | Unit Price of goods on product tray 2 | Name of goods on product tray 2 | Initial weight of goods on product tray 2 | ... |
| Load cell ID3 of product tray 3 | Unit Price of goods on product tray 3 | Name of goods on product tray 3 | Initial weight of goods on product tray 3 | ... |
| ... | ... | ... | ... | ... |

The data storage 9026 stores the identification, unit price and initial weight information for products (i.e., goods) on each product tray. The identification for each product is used as indices to the corresponding unit price and initial weight information. The identification and unit price information are entered when initializing the system, and the initial weight is updated as the most recently detected weight on the tray by the load cells.

The door lock sensor 9028 is connected to the central processing unit 9020 and sends real-time detection of door status change to the central processing unit 9020. Having detected that the door is closed, the central processing unit 9020 performs the following operations:

(1) Reading the current remaining weight of goods on a product tray.

(2) Reading the unit price and the initial weight of the goods in the product tray according to their identifications.

(3) Subtracting the current remaining weight obtained in step (1) from the initial weight obtained in step (2) to get the weight of goods taken.

(4) Multiplying the weight of goods taken, which is obtained in step (3), by the unit price obtained in step (2) to get the amount due.

(5) Updating the initial weight in the data storage using the most recently detected weight on the tray, which is obtained in step (1).

(6) Repeating steps (1)-(5) until the amount due for each product tray is determined and the initial weight information for each product tray is updated.

(7) Summing all obtained amounts in step (6) to get the total amount due for this purchase. Displaying the amount due information to customers and controlling the electromagnetic lock driver to lock the cabinet door once it is closed. The payment information will be transmitted by the transceiver 9025 to the cloud-based operation and accounting platform, allowing it to complete the payment process via password-less authentication.

The display unit 3001 is connected to the central processing unit 9020 and may be used to indicate or display the payment information, the unit price, the operation instruction, the connection status, or commercials. The display unit 3001 may also display a QR code to be scanned. The alarm 9029 is connected to the central processing unit and may be used to generate alerts when being instructed by the central processing unit. The electromagnetic lock driver 9027 is connected to the central processing unit and may be used to lock or unlock the electromagnetic lock 3006 according to the instructions from the central processing unit. The transceiver 9025 is connected to the central processing unit and may be used to transmit external signals, like the QR code signal or the completion-of-payment signal, from the operation and accounting platform 9021 to the central processing unit 9020. It may also transmit the payment information from the central processing unit 9021 to the operation and accounting platform 9021. The central processing unit 9020 is connected to a remote cloud-based server 9100, which monitors the operation of the vending apparatus remotely and updates the unit price and product name in the data storage 9026.

The present invention comprises the operation and accounting platform 9021, which is connected to the self-checkout vending apparatus wirelessly. The display unit 3001 may be equipped with a QR code or a QR code reader, enabling the communication with the operation and accounting platform 9021. The operation and accounting platform 9021 is a cloud-based service platform, such as WeChat or Alipay, that comprises the accounting module 9022 and the operation identification module 9023. The operation identification module 9023 is used to confirm the identification of customers by their operation terminals like mobile devices. The operation and accounting module 9023 is wirelessly connected to the transceiver 9025. The wireless transceiver 9025 connects the central processing unit 9020 to the external platforms. When customers scan the QR code or use the QR code reader with their mobile devices, the operation identification module 9023 confirms the customers' identification to the transceiver, which then transmits the confirmation information to the central processing unit 9020. The central processing unit then drives the electromagnetic lock driver 9027 to unlock the door 3008 so that customers can get the goods that are in stock in the vending apparatus. The payment information generated by the central processing unit 9020 is transmitted to the accounting module 9022 by the transceiver 9025. The accounting module 9022 then settles the payment via password-less authentication or displays the payment information to customers, allowing them to pay online. When the payment is received, the accounting module 9022 sends the confirmation and transaction details to the transceiver 9025, which forwards the information to the central processing unit 9020. The central processing unit 9020 stores the transaction details in the data storage 9026. Further, the self-checkout vending apparatus may be equipped with a card reader to support the traditional payment via debit or credit cards. The card reader, if included, is connected to the transceiver 9025 so that the payment can be via the card reader and the locking or unlocking of the cabinet door 3007 is dependent on the status of the card reader.

An exemplary operation of the present invention will be explained as follows. Each product tray holds goods (for example, fruits or vegetables) with same unit price. The load cell IDs, the unit price information, the names of the goods (optional) and the initial weights are entered into the system after replenishment. A customer may scan the QR code using his/her mobile device or use the QR code reader to scan his/her payment app code. The operation identification module 9023 of WeChat or Alipay then confirms the customer' ID and sends a confirmation to the transceiver, when transmits the confirmation to the central processing unit 9020. Upon receiving the confirmation, the central processing unit 9020 first determines if goods in the vending apparatus is out of stock by reading the weight measurement from each product tray and check if they are all zeros. If they are, the central processing unit 9020 triggers an alarm and show an out-of-stock alert on the display unit 3001. Otherwise, the central processing unit 9020 drives the electromagnetic lock driver 9027 to unlock the cabinet door 3007 so that customers may get the goods they want. The load cells sense the real-time weight data change during the customer operation and update the measurements to the central processing unit 9020. When finished, the customer may close the door manually. To remind that customer of closing the door after taking the desired goods, a voice reminder will be announced by the alarm during the customer operation. After closing the door, the door lock sensor updates the action to the central processing unit, which then performs the following operations:

(a) Reading the current remaining weight on a product tray.

(b) Reading the unit price and initial weight information of the goods according to the product tray's corresponding load cells ID.

(c) Subtracting the current remaining weight obtained in step (a) from the initial weight obtained in step (b) to get the weight of goods sold.

(d) Multiplying the weight of goods sold, which is obtained in step c), by the unit price obtained in step (b) to get the amount due.

(e) Updating the initial weight in the data storage using the most recently detected weight on the product tray, which is obtained in step (a).

(f) Repeating steps (a)-(e) until the amount due for each product tray is determined and the initial weight information for each product tray is updated in the data storage.

(g) Summing all the obtained amount dues in step (f) to get the total amount due for this purchase. Displaying the amount due information to customers and controlling the electromagnetic lock driver to lock the cabinet door once it is closed. The payment information will be transmitted by the transceiver to the cloud-based operation module, allowing it to settle the payment via password-less authentication. The details are then sent by the accounting and operation module to the central processing unit, which stores the details in the data storage. The accounting and operation module will display the details to customers in their WeChat account. Customers may also track their expense details and history by following the retail company's official WeChat account, wherein the retail company operates the vending apparatus.

A self-checkout vending apparatus in accordance with any one of the above three embodiments applies a weighing by difference approach, wherein the weight of goods sold is the difference between the weights on a weighing scale before and after a customer taking a desired amount of goods, and this weight of goods sold is multiplied by the unit price of the goods to obtain the total cost of the purchase.

The present invention connects a cloud-based server and consumer devices in operation, allowing monitor and control of the vending apparatuses remotely. By equipping the vending apparatus with a code scan area, the opening/closing of the product access window as well as the payment can be performed automatically, which largely simplifies the customer operation.

F. Conclusion

The present invention presents a nutrition tracking system that enables customers to easily track and team their diet and nutrition intake. The nutrition tracking system further comprises a plurality of weight-based food offering terminals and nutrition and meal information inquiry terminals. The weight-based food offering terminal may be a weight-based self-checkout apparatus offering food. Three embodiments of weight-based self-checkout apparatuses are described in detail. Furthermore, weight-based food offering terminals may be installed in food service carts, especially those that deliver meals in hotels, hospitals, sanatoriums, and other healthcare facilities.

While various embodiments of the present invention have been described above, it should be understood that they have been presented by way of examples, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A nutrition tracking system comprising a nutrition tracking server and a weight-based food offering terminal,
    wherein the weight-based food offering terminal further comprises a display and a data storage;
    wherein the data storage stores a name and a unit price for a type of food and an initial weight of the food; the weight-based food offering terminal automatically performs the following steps:
    (a) measuring a weight of food taken by a customer or for a customer based on the initial weight;
    (b) calculating a cost of food taken;
    (c) showing the weight and the cost on the display in real time;
    (d) if detecting more food is taken, repeating steps (a) to (c);
    (e) upon receiving a completion signal, generating a vending information record and sending the vending information record to the nutrition tracking server.

2. The system of claim 1, wherein the vending information record comprises an identification of the customer, a name of the type of food, the weight of the food taken, and a vending time.

3. The system of claim 1, wherein the vending information record comprises an identification of the customer, an identification of the weight-based food offering terminal, the weight of the food taken, and a vending time.

4. The system of claim 3, wherein the vending time is the time when the cost of food is paid.

5. The system of claim 1, wherein the weight-based food offering terminal receives an identification of the customer trigger by a user scan activity before performing step (a).

6. The system of claim 1, wherein step (e) further comprising using current weight of remaining food in the weight-based food offering terminal to update the initial weight.

7. The system of claim 1, wherein the nutrition tracking server comprises a customer meal database; wherein the nutrition tracking server receives vending information records from a plurality of weight-based food offering terminals, generates customer meal information entries by combining vending information records associated with same customer identification, stores the customer meal information entries in the customer meal database, and updates the customer meal database.

8. The system of claim 7, wherein the nutrition tracking server further comprises a customer nutrition database; the nutrition tracking server analyzes the received vending information records and generates customer nutrient intake information to be stored in the customer nutrition database.

9. The system of claim 8 further comprising a nutrition and meal information inquiry terminal.

10. The system of claim 9, where in the nutrition and meal information inquiry terminal is integrated into a mobile device.

11. The system of claim 1, wherein the weight-based food offering terminal further comprises a weight by difference scale.

12. The system of claim 5, wherein the user scan activity comprises a QR code.

13. The system of claim 5, wherein the user scan activity comprises a card reader.

14. The system of claim 1 further comprising a plurality of weight-based food offering terminals, and one or more of the weight-based food offering terminals are on a food service cart.

15. The system of claim 14, wherein the one or more weight-based food offering terminals on the food service cart share a same network communication module.

16. The system of claim 9, wherein the nutrition and meal information inquiry terminal sends an inquiry and receives a user's meal information.

17. The system of claim 9, wherein the nutrition and meal information inquiry terminal sends an inquiry and receives a user's meal and nutrition information during a time period.

* * * * *